(12) United States Patent
Kobayashi et al.

(10) Patent No.: US 11,167,119 B2
(45) Date of Patent: Nov. 9, 2021

(54) MICRONEEDLE PATCH APPLICATOR AND HOUSING FOR SAME

(71) Applicant: MEDRX CO., LTD., Higashikagawa (JP)

(72) Inventors: Katsunori Kobayashi, Higashikagawa (JP); Hidetoshi Hamamoto, Higashikagawa (JP)

(73) Assignee: MEDRX CO., LTD., Higashikagawa (JP)

( * ) Notice: Subject to any disclaimer, the term of this patent is extended or adjusted under 35 U.S.C. 154(b) by 613 days.

(21) Appl. No.: 16/062,671

(22) PCT Filed: Dec. 20, 2016

(86) PCT No.: PCT/JP2016/087965
§ 371 (c)(1),
(2) Date: Jun. 15, 2018

(87) PCT Pub. No.: WO2017/110815
PCT Pub. Date: Jun. 29, 2017

(65) Prior Publication Data
US 2018/0361132 A1 Dec. 20, 2018

(30) Foreign Application Priority Data

Dec. 21, 2015 (WO) .................. PCT/JP2015/085707
Aug. 12, 2016 (JP) .............................. JP2016-158930

(51) Int. Cl.
*A61M 37/00* (2006.01)
*A61K 9/00* (2006.01)

(52) U.S. Cl.
CPC ........ *A61M 37/0015* (2013.01); *A61M 37/00* (2013.01); *A61K 9/0021* (2013.01);
(Continued)

(58) Field of Classification Search
CPC .............. A61M 37/0015; A61M 37/00; A61M 2037/0023; A61M 2037/0053; A61K 9/0021
(Continued)

(56) References Cited

U.S. PATENT DOCUMENTS 6,537,242 B1 3/2003 Palmer
6,743,211 B1 6/2004 Prausnitz et al.
(Continued)

FOREIGN PATENT DOCUMENTS

JP 2005-527249 A 9/2005
JP 2006149818 A 6/2006
(Continued)

OTHER PUBLICATIONS

Extended European Search Report issued in corresponding European Patent Application No. 16878704.2, dated Jun. 4, 2019 (7 pages).
(Continued)

*Primary Examiner* — Phillip A Gray
(74) *Attorney, Agent, or Firm* — Buchanan Ingersoll & Rooney PC

(57) ABSTRACT

The purpose of the present application is to provide a microneedle patch applicator and a microneedle patch applicator housing, whereby perpendicular penetration properties of the needle into skin are enhanced. A microneedle patch applicator housing has a flat peripheral base part configured from a single sheet or film, and a protruding part which is surrounded by the peripheral base part and bulges perpendicularly upward toward a top surface from a bottom surface with respect to the peripheral base part. A bottom-surface portion of the protruding part constitutes part of a microneedle patch support surface. The protruding part is provided with a plurality of recessed fold parts, and the
(Continued)

recessed fold parts have recess bottoms oriented in the direction away from a center part of the protruding part.

20 Claims, 21 Drawing Sheets

(52) U.S. Cl.
CPC ............... *A61M 2037/0023* (2013.01); *A61M 2037/0053* (2013.01)

(58) Field of Classification Search
USPC ........................................................ 604/173
See application file for complete search history.

(56) References Cited

U.S. PATENT DOCUMENTS

| | | | |
|---|---|---|---|
| 8,821,446 B2* | 9/2014 | Trautman | A61M 37/0015 |
| | | | 604/173 |
| 2002/0032415 A1 | 3/2002 | Trautman et al. | |
| 2002/0091357 A1 | 7/2002 | Trautman et al. | |
| 2008/0195035 A1 | 8/2008 | Frederickson et al. | |
| 2009/0157041 A1 | 6/2009 | Pettis et al. | |
| 2009/0198189 A1 | 8/2009 | Simons et al. | |
| 2011/0276027 A1 | 11/2011 | Trautman et al. | |
| 2012/0184916 A1 | 7/2012 | Kobayashi et al. | |
| 2013/0006187 A1 | 1/2013 | Kobayashi et al. | |
| 2016/0121092 A1 | 5/2016 | Kato | |

FOREIGN PATENT DOCUMENTS

| | | | |
|---|---|---|---|
| JP | 2008520369 | A | 6/2008 |
| JP | 2008535587 | A | 9/2008 |
| JP | 2008543528 | A | 12/2008 |
| JP | 2010516337 | A | 5/2010 |
| JP | WO2009107806 | A1 | 7/2011 |
| JP | WO2011089907 | A1 | 7/2011 |
| JP | 2013-027492 | A | 2/2013 |
| JP | 2014-042788 | A | 3/2014 |
| WO | 2006055795 | A1 | 5/2006 |
| WO | 2006108185 | A1 | 10/2006 |
| WO | 2007002522 | A1 | 1/2007 |
| WO | 2008091602 | A2 | 7/2008 |
| WO | 2011016230 | A1 | 2/2011 |
| WO | 2015005143 | | 1/2015 |

OTHER PUBLICATIONS

The extended European Search Report dated Oct. 14, 2020, by the European Patent Office in corresponding European Application No. 20180240.2. (8 pages).

* cited by examiner (A)

(B)

(C)

(A)

(B)

(A)

(B)

(A)

(B)

(a)

(b)

MICRONEEDLE PATCH APPLICATOR AND HOUSING FOR SAME

TECHNICAL FIELD

The present invention relates to a microneedle patch applicator that applies a microneedle patch to skin of animals (including human beings and animals other than human beings). The present invention relates also to a microneedle patch applicator housing.

BACKGROUND ART

Recent attention has been given to a drug administration system using a drug-coated microneedle patch as one of percutaneously absorbed drug administration systems (see Patent Documents 1 to 7). This microneedle patch has, on its base material, densely formed thin protuberances or needles of several hundred microns in length. The needles carrying target drug (vaccine, protein, or molecules such as peptide) thereon or therein are stuck into skin to directly transport the drug to dermis or epidermis. The microneedle patch has a number of advantages such as not imposing a burden on the liver unlike oral medicines, not inducing a pain by penetration of the needle unlike injections, and being able to reduce side effects caused by transient excess absorption of drug.

The needles of the microneedle patch are each extremely thin (approx. several tens of microns in root diameter). Therefore, the needles may possibly be damaged or broken by the resistance upon penetration into skin. In the case of needles made of a metal (e.g. titanium), indwelling risk arising from intracutaneous breakage is a significant problem. Needles made of a biodegradable resin may be damaged or broken more easily than the metal needles. In particular, if the needles are tilted with respect to skin, insertability of needles into skin lowers or the needles become easy to break due to a bending force acting thereon. Thus, there is a need for means enabling the needles to be punctured vertical to skin and ensuring secure application of the microneedle patch to skin.

PRIOR ART DOCUMENT

Patent Document

Patent Document 1: JP-A-2006-149818
Patent Document 2: JP-T-2008-520369
Patent Document 3: JP-T-2008-543528
Patent Document 4: JP-T-2008-535587
Patent Document 5: JP-T-2010-516337
Patent Document 6: JP-Re-2009-107806
Patent Document 7: JP-Re-2011-089907

SUMMARY OF THE INVENTION

Problem to be Solved by the Invention

The present invention provides a microneedle patch applicator and a microneedle patch applicator housing, capable of enhancing the vertical penetration properties of needles relative to skin and ensuring secure application of a microneedle patch onto skin.

Means for Solving Problem

In an embodiment of a microneedle patch applicator housing according to the present invention,
the housing is formed from a single sheet or film having a top surface and an undersurface and comprises a flat peripheral base part and a raised part surround by the peripheral base part and bulging vertically, with respect to the peripheral base part, from the undersurface toward the top surface, an undersurface portion of the raised part forms a surface supporting a microneedle patch, the raised part includes a plurality of concavely bent parts, and the concavely bent parts each have a concave bottom toward a direction away from a center portion of the raised part.

In another embodiment of the microneedle patch applicator housing, the concavely bent parts are arranged symmetrically with respect to two horizontal axes (x-axis and y-axis) that are orthogonal to a vertical axis (z-axis) extending through a center of the raised part and that are orthogonal to each other.

In another embodiment of the microneedle patch applicator housing, the concavely bent parts are arranged with a rotational symmetry (n-fold symmetry: n is an integer greater than or equal to 2).

In another embodiment of the microneedle patch applicator housing, the raised part is shaped symmetrical with respect to at least one of the two horizontal axes (x-axis and y-axis).

In another embodiment of the microneedle patch applicator housing, the raised part is shaped symmetrical with respect to the two horizontal axes (x-axis and y-axis).

In another embodiment of the microneedle patch applicator housing, the raised part is shaped with a long axis (x-axis) that is one of the two horizontal axes (x-axis and y-axis) and with a short axis (y-axis) that is the other of the two horizontal axes.

In another embodiment of the microneedle patch applicator housing, the raised part is rotationally symmetrical (n-fold symmetry: n is an integer greater than or equal to 2) with respect to a vertical axis (z-axis) extending through a center of the raised part.

In another embodiment of the microneedle patch applicator housing, the raised part has at a center a recess, an undersurface portion of which forms a surface supporting the microneedle patch.

In another embodiment of the microneedle patch applicator housing, it comprises a ridge extending along a contour of the raised part and surrounding the recess, the ridge including a plurality of concavely bent parts.

In another embodiment of the microneedle patch applicator housing, the contour is shaped symmetrical with respect to the two horizontal axes (x-axis and y-axis).

In another embodiment of the microneedle patch applicator housing, the contour is shaped with a long axis (x-axis) that is one of the two horizontal axes (x-axis and y-axis) and with a short axis (y-axis) that is the other of the two horizontal axes.

In another embodiment of the microneedle patch applicator housing, the contour is rotationally symmetrical (n-fold symmetry: n is an integer greater than or equal to 2) with respect to the vertical axis (z-axis).

In another embodiment of the microneedle patch applicator housing, the recess includes a flat surface, the flat surface having two easy-to-deform parts that are arranged symmetrically with respect to the short axis and that extend parallel to the short axis (y-axis), the flat surface including a center region interposed between the two easy-to-deform parts and end regions positioned on both sides of the center region.

In another embodiment of the microneedle patch applicator housing, the raised part is disposed continuously circumferentially around the vertical axis (z-axis).

In another embodiment of the microneedle patch applicator housing, the raised part is disposed discontinuously circumferentially around the vertical axis.

In another embodiment of the microneedle patch applicator housing, at least one or more of the plurality of concavely bent parts have a concave bottom sloped downward toward a direction away from a center portion of the raised part.

An embodiment of a microneedle patch applicator according to the present invention comprises:
the microneedle patch applicator housing of any one of the above; and
a microneedle patch supported on a surface that supports the microneedle patch.

In another embodiment of the microneedle patch applicator, the recess comprises a finger hold.

In an embodiment of the microneedle patch applicator,
a protective sheet is affixed to an undersurface of the housing,
the protective sheet closing an opening of a microneedle patch storage space formed at the back of the raised part.

In another embodiment of the microneedle patch applicator,
the finger hold comprises an indicator indicating that a predetermined force is applied to the finger hold.

Effect of the Invention

According to the microneedle patch applicator and the housing for the same in accordance with the present invention, when the raised part is pressed, the patch carried on the back surface thereof deforms vertically and deeply relative to skin. As a result, the entirety of the patch is vertically pressed against skin with a uniform force. This allows the needles disposed on the patch to penetrate vertically into skin so that the needles cannot be bend, damaged, or broken at the time of puncture.

MODES FOR CARRYING OUT THE INVENTION

Embodiments of a microneedle patch applicator and a microneedle patch applicator housing according to the present invention will now be described with reference to the accompanying drawings.

First Embodiment

Figure 1:
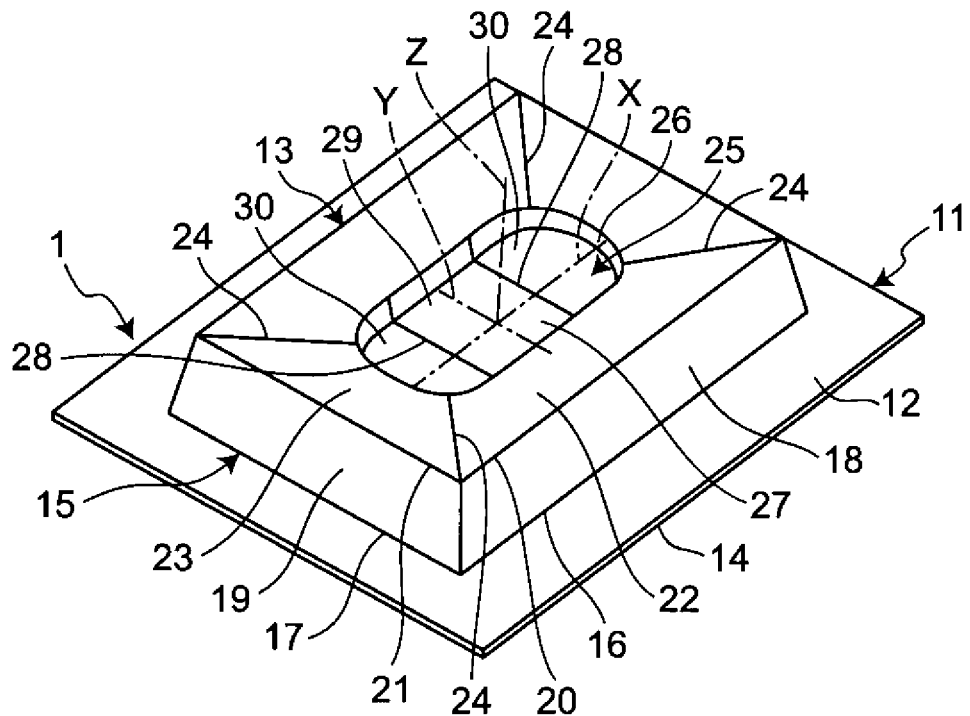
FIG. 1 is a perspective view, from diagonally above, of a microneedle patch applicator and a housing for the same according to a first embodiment.

FIG. 1 shows a microneedle patch applicator (hereinafter, referred to as "applicator") 1 according to a first embodiment.

The applicator 1 comprises a container or housing 11 that houses a microneedle patch 40 (see FIG. 6) that will be described later.

The housing 11 is formed (e.g. vacuum forming, pressure forming, or press forming) for example from a thin resin sheet or film or molded (e.g. injection molding) from a molten resin injected into a cavity of a mold and has an external shape shown. A material suitable for forming or molding of the housing is desirably a material having a flexibility and easy to be bent, deformed or restored and can be for example a resin such as polyethylene, polypropylene, polyethylene terephthalate, polystyrene, nylon, acrylic, silicone, or ABS resin. Unless the above characteristics such as flexibility are impaired, these resins may contain a hygroscopic agent and/or an oxygen absorber, etc. so as to impart hygroscopic and/or oxygen absorbing functions thereto. The thicknesses of parts of the housing are properly determined such that a desired deformation described later occurs when the housing 11 is pressed from above with a human finger. It is desirable that the housing have a feature of easily bending at a concavely bent part that will be described later. For example, in the case of the housing made of polyethylene, polypropylene, or polyethylene terephthalate, the thicknesses of parts are preferably approx. 50 µm to 1 mm, more preferably 100 µm to 500 µm.

The housing 11 comprises a flat plate-like peripheral base part 12 and a raised part 13 that is surround by the peripheral base part 12 and that is raised upward (in z-axis direction of FIG. 1) from the peripheral base part 12. The peripheral base part 12 is surrounded by a substantially rectangular outer edge 14. The raised part 13 has a substantially rectangular contour 15 that is substantially similar to the rectangular outer edge 14 of the peripheral base part 12. In the embodiment, the contour 15 includes a pair of long-side-direction contour parts 16 extending in the long-side direction (x-axis direction of FIG. 1) of the rectangular peripheral base part 12 and a pair of short-side-direction contour parts 17 extending in the short-side direction (y-axis direction of FIG. 1) thereof.

The raised part 13 has a substantially truncated pyramid shape and comprises a long-side-direction side wall 18 and a short-side-direction side wall 19 which extend upward from the long-side-direction contour part 16 and the short-side-direction contour part 17, respectively. The long-side-direction side wall 18 and the short-side-direction side wall 19 may be tilted inward. A top of the raised part 13 includes a long-side-direction tilted top-surface portion 22 and a short-side-direction tilted top-surface portion 23 which extend from an upper end 20 of the long-side-direction side wall 18 and an upper end 21 of the short-side-direction side wall 19, respectively, toward a center of the raised part 13. Preferably, the long-side-direction tilted top-surface portion 22 and the short-side-direction tilted top-surface portion 23 are downward tilted inward from the upper end 20 and the upper end 21, respectively.

The long-side-direction tilted top-surface portion 22 and the short-side-direction tilted top-surface portion 23 are in contact with each other at a boundary extending in a direction which forms a predetermined angle (e.g. approx. 45 degrees) relative to the upper end 20 of the long-side-direction side wall 18 and the upper end 21 of the short-side-direction side wall 19, respectively, when the raised part 13 is viewed from above. Since the long-side-direction tilted top-surface portion 22 and the short-side-direction tilted top-surface portion 23 are each tilted diagonally downward toward the center of the raised part 13 as described above, the boundary forms a concavely bent part 24. The part of the concavely bent part 24 may be thinner than the right and left regions (the top-surface portions 22 and 23) or may have a U-shaped or inverted U-shaped section.

The raised part 13 has a recess 25 at the center thereof. The recess 25 includes a circumferential wall 26 extending downward from inner edges of the long-side-direction tilted top-surface portion 22 and the short-side-direction tilted top-surface portion 23 and a substantially flat bottom 27 connected to a lower end of the circumferential wall 26.

As shown, the recess 25 is in the shape of a track when viewed from above. The bottom 27 of the recess 25 includes two easy-to-deform parts 28 extending in the short-side direction. As shown, the easy-to-deform parts 28 are arranged symmetrically with respect to a center (an intersection of X-axis, Y-axis, and Z-axis shown) of the recess 25 so that end regions 30 on both sides of a center region 29 interposed between the two easy-to-deform parts 28 can easily bend upward from the center region 29. The easy-to-deform part 28 may be in the form of a thinned portion that is thinner than the other portions or a deformed portion having a section bent into U shape or inverted-U shape.

Figure 3:
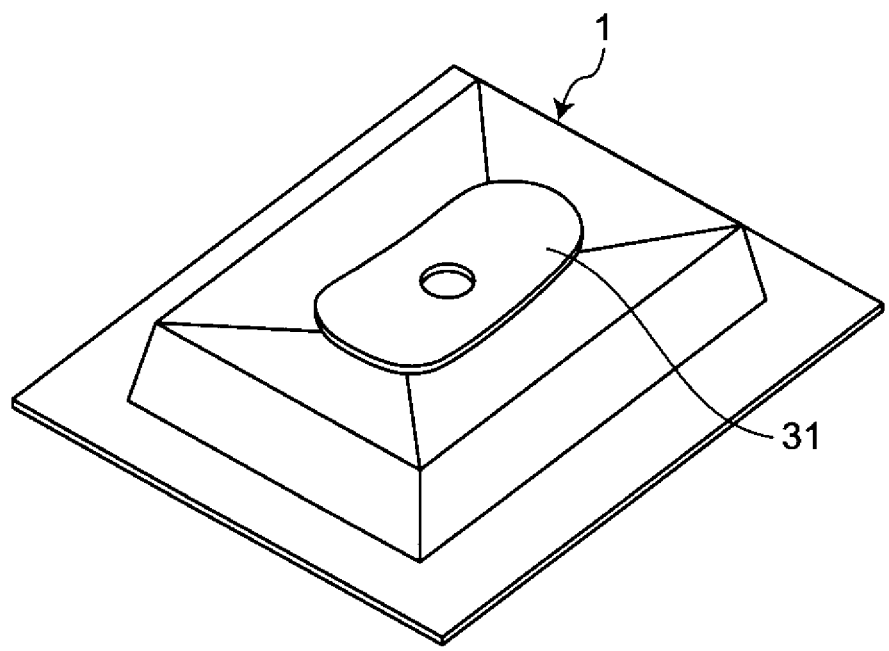
FIG. 3 is a perspective view, from diagonally above, of the microneedle patch applicator having a finger hold and the housing for the same.

In the embodiment, as shown in FIG. 3, the recess 25 of the raised part 13 may comprise a finger hold (a pressed portion) 31 against which the user presses his/her finger upon operation. The finger hold 31 has a contour substantially equal to or slightly smaller than the contour of the recess 25.

Figure 4:
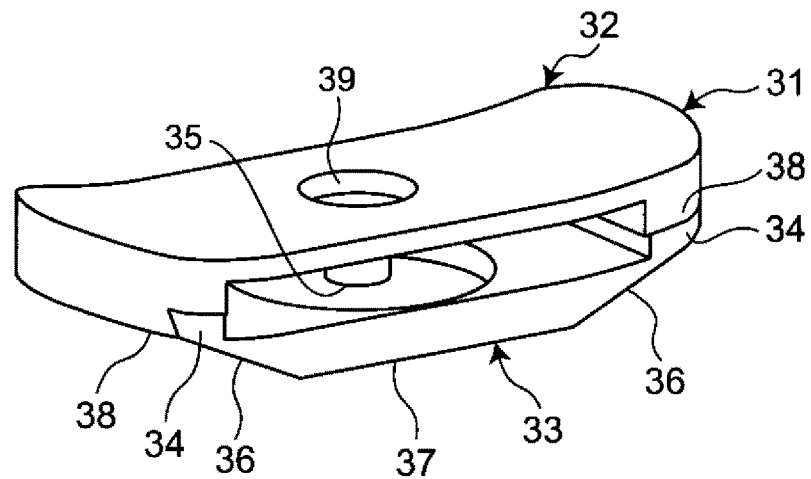
FIG. 4A is a perspective view of the finger hold.
FIG. 4B is a plan view of the finger hold.
FIG. 4C is a front view of the finger hold.
Figure 4:
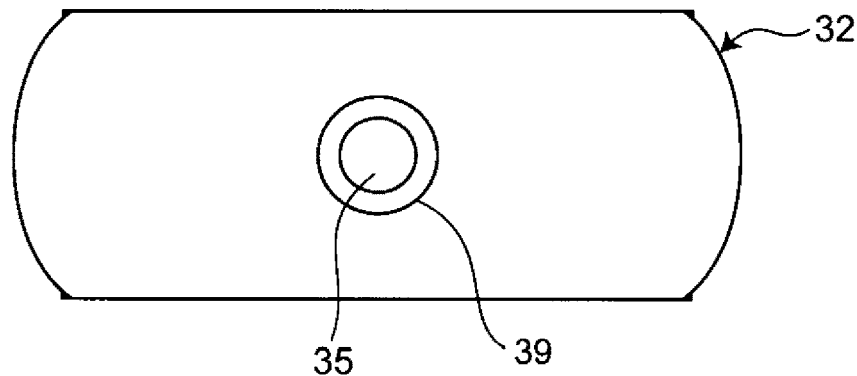
Figure 4:
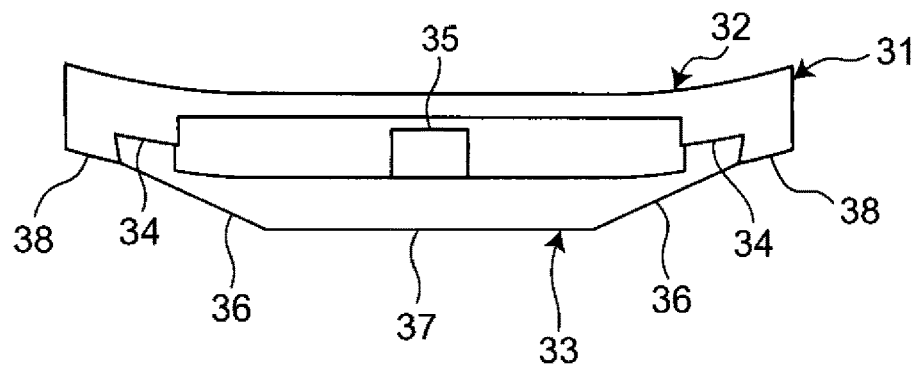

As shown in FIG. 4, the finger hold 31 comprises an upper member 32 and a lower member 33. When viewed from above, the upper member 32 has the shape of a track substantially equal in size to the recess 25. The lower member 33 has, at both ends in the longitudinal direction (near an arcuate portion), a support 34 protruding upward from the top of the lower member 33. The lower member 33 has, at its center, a boss (protrusion) 35 protruding upward from the top thereof. In the embodiment, the boss 35 is of a cylindrical shape. A bottom of the lower member 33 is a slant surface that includes end regions 36 extending diagonally upward from edges of a center region 37. Accordingly, when the finger hold 31 is stored in the recess 25, only the center region 37 of the lower member 33 is in contact with the center region 29 of the recess bottom 27, with the end regions 36 of the lower member 33 being spaced apart from the end regions 30 of the recess bottom 27.

Corresponding to the support 34 of the lower member 33, the upper member 32 comprises a pair of protuberances 38 protruding downward from the bottom of the upper member 32. The position pf the protuberance 38 is determined such that the upper member 32 is positioned with respect to the lower member 33 so that an inner edge of the protuberance 38 lies at an outer edge of the support 34 when the upper member 32 is assembled on the lower member 33. The upper member 32 has at its center a through-hole 39 extending vertically. It is preferred that the cross-section of the through-hole 39 be greater than or slightly greater than the cross-section of the boss 35 of the lower member 33. The position of the through-hole 39 is determined such that, when the upper member 32 is assembled on the lower member 33, the boss 35 and the through-hole 39 are coaxial and vertically confront each other.

Various conditions of the upper member 32 and the lower member 33 (e.g. materials making up the upper material 32 and the lower material 33, the thicknesses thereof, and the height of the boss 35) are determined such that, when a finger is abutted against the top of the upper member 32 to apply a predetermined pressing force (that will be described later) thereto, the upper member 32 flexes at its center portion downward with respect to the both-side portions thereof, or that the lower member 33 flexes at its center portion relatively upward with respect to the both-side portions thereof, or that the upper member 32 and the lower member 33 flexes at their respective center portions downward and upward, respectively, so that the boss 35 passes through the through-hole 39 of the upper member 32 to protrude from its top by a predetermined length to abut against the finger. It is therefore preferred that elastic materials allowing such deformations be selected as the materials of the upper member 32 and the lower member 33.

The thus configured finger hold 31 is disposed in the recess 25, with the upper material 32 and the lower material 33 combined. The combined upper member 32 and lower member 33 may be adhered to each other by an adhesive or may be integrally molded. The center region 37 of the lower member undersurface and the recess bottom center region 29 confronting the center region 37 may be adhered to each other by an adhesive or a double-sided tape. The finger hold 31 need not be mounted in advance on the housing 11 and the finger hold 31 may be mounted in advance in the recess 25 before use of the applicator 1.

Figure 5:
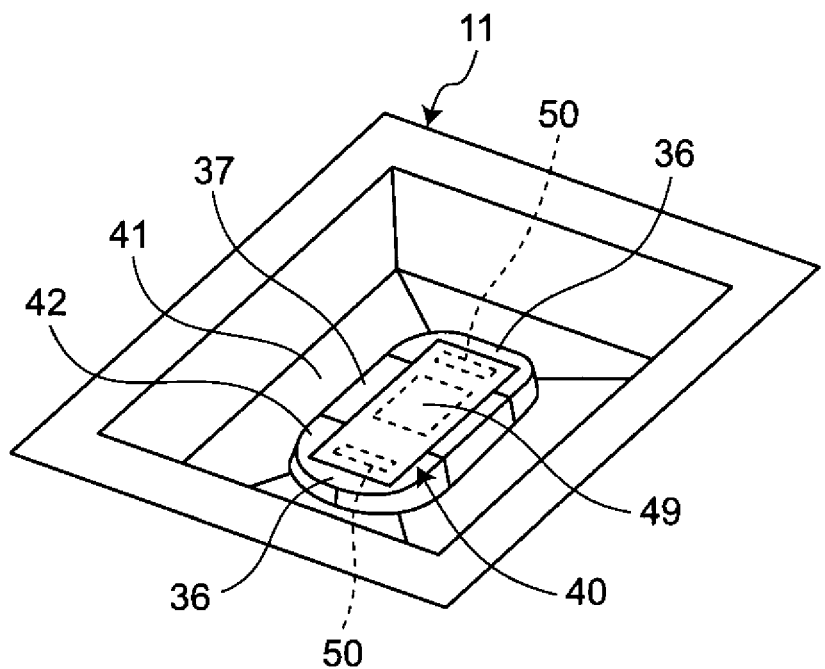
FIG. 5 is a perspective view, from diagonally below, of the microneedle patch applicator having a microneedle chip and the housing for the same.

As shown in FIG. 5, a microneedle patch (hereinafter, referred to as "patch") 40 is stored in a patch storage space 41 formed on the back surface of the raised part 13 and is secured to a patch support surface 42 configured by the back surface of the recess 25.

Figure 6:
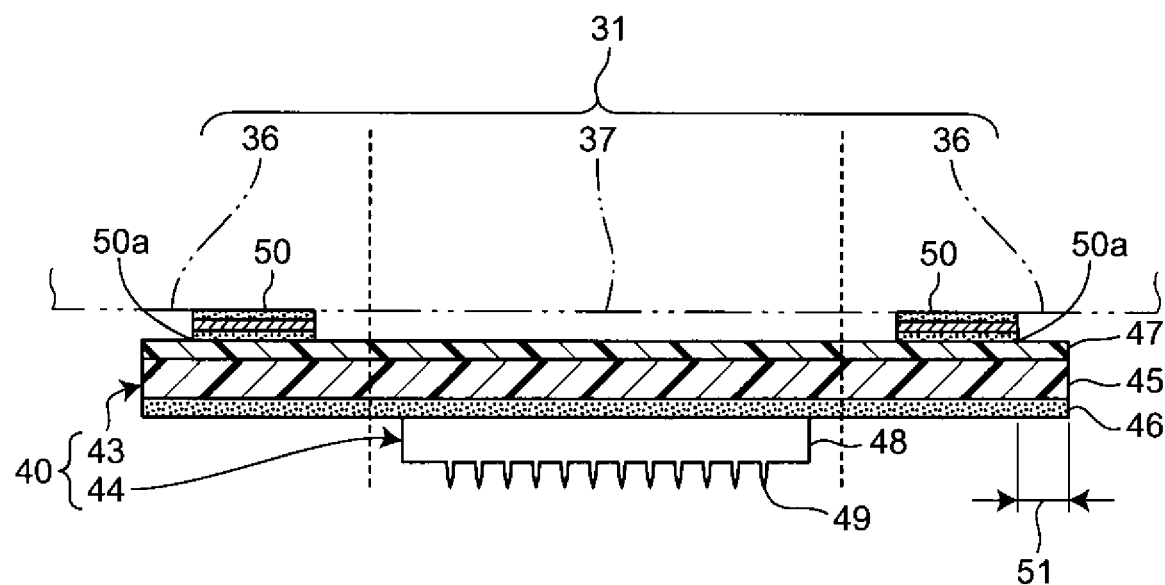
FIG. 6 is a schematic enlarged sectional view of a microneedle patch.

In general, as shown in FIG. 6, the patch 40 comprises a sheet substrate 43 and a microneedle array 44 supported thereby. The sheet substrate 43 includes a substrate film 45, a pressure-sensitive adhesive layer 46 disposed on an undersurface of the substrate film 45 (a support surface of the microneedle array 44), and a release treatment layer (a release layer) 47 disposed on a top surface of the substrate film 45 (a surface confronting the patch support surface 42). The microneedle array 44 includes a quadrangular (or circular) base layer 48 and a multiplicity of elongated needles 49 of a predetermined height (e.g. 300 to 1000 micrometer) arranged regularly at predetermined intervals (e.g. 300 to 1000 micrometer) in lattice or in honeycomb on an undersurface of the base layer 48. The microneedle array 44 is made by filling, for example, a biodegradable synthetic polymer material (e.g. hyaluronic acid, collagen, polylactic acid, or polyglycolic acid) into a mold of a corresponding shape. Although not shown, the needle 49 is coated at its tip side with a target drug (vaccine, protein, or molecules such as peptide). Alternatively or additionally, in the case of making the microneedle array 44 of a biodegradable resin, the target drug may be contained in the interior of the needle 49 upon molding thereof.

The sheet substrate 43 and the microneedle array 44 are integrated by adhering the base layer 48 of the microneedle array 44 onto the pressure-sensitive adhesive layer 46 of the sheet substrate 43. As shown in FIGS. 5 and 6, the sheet substrate 43 is larger than the microneedle array 44. Accordingly, when the microneedle array 44 is adhered to the sheet substrate 43, a sufficient area of pressure-sensitive adhesive layer 46 is exposed around the microneedle array 44.

The thus formed patch 40 is adhered to the patch support surface 42 by use of a double-sided tape 50. When adhered, the microneedle array 44 lies in the patch support surface center region 37 corresponding to the recess center region 29 while the double-sided tapes 50 on both sides lies in the patch support surface end regions 36 corresponding to the recess end regions 30.

The double-sided tape 50 serves to temporarily hold the patch 40 on the patch support surface 42 prior to adhesion of the patch 40 onto skin. After adhesion of the patch 40 onto skin, the patch 40 need to be held on skin, apart from the housing 11. It is therefore preferred that conditions (size, shape, attachment position, adhesive force) of the double-sided tape 50 be determined such that the adhesive force of the double-sided tape 50 to the release treatment layer (release layer) 47 be less than the adhesive force of the pressure-sensitive adhesive layer 46 to skin. Specifically, as shown, the double-sided tape 50 is preferably attached to positions displaced inward by a predetermined distance (designated at reference numeral 51 in FIG. 6) from both ends of the sheet substrate 43 so that, when removing the housing 11 from skin after adhesion of the patch 40, the double-sided tape 50 can be released gradually from the release treatment layer 47, inwardly from the outer edges 50a. The double-sided tape 50 may be replaced by an adhesive.

Figure 2:
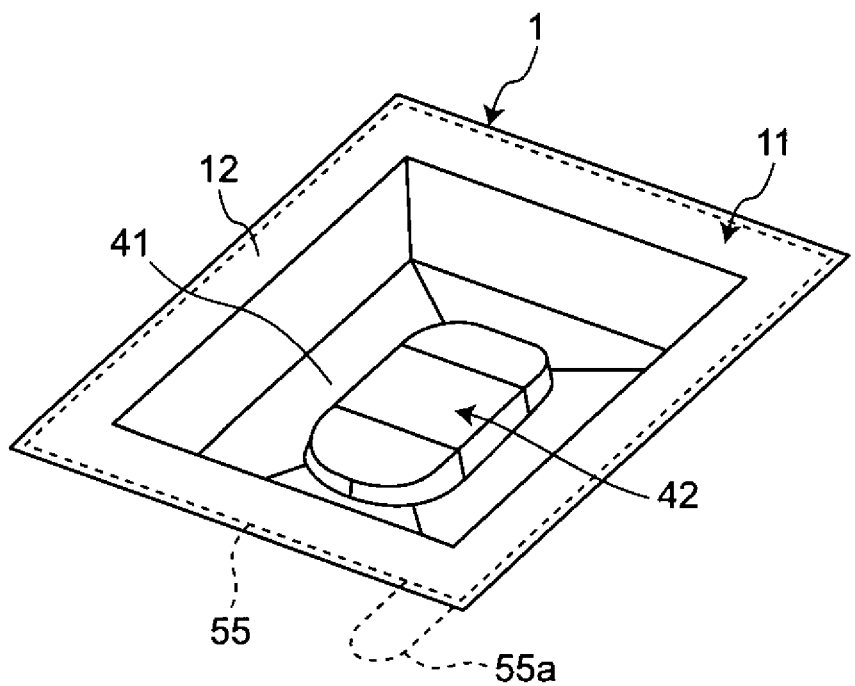
FIG. 2 is a perspective view, from diagonally below, of the microneedle patch applicator and the housing for the same shown in FIG. 1.

In order to protect the patch 40 stored in the patch storage space 41, as shown by a broken line in FIG. 2, a protective sheet 55 of a size enough to close the opening of the patch storage space 41 is preferably attached to the undersurface of the housing 1. It is preferred that the size of the protective sheet 55 be substantially equal to the contour of the housing 11. Preferably, the protective sheet 55 includes a tab 55a caught by the user when the protective sheet 55 is released from the housing 11. The patch storage space 41 may hermetically contain, in its interior, agents such as a moisture absorbent and an oxygen absorbent for suppressing degradation of the microneedles and of drug carried thereon.

Usage of the thus configured applicator 1 will be described.

The protective sheet 55 affixed to the bottom surface of the housing 11 is first peeled off to expose the patch 40.

The applicator is then placed on skin such that the peripheral base part 12 of the housing 11 abuts against skin.

Subsequently, a finger (a thumb for example) is abutted on the top surface of the finger hold 31 to press the applicator 1 against skin. This allows the raised part 13 of the housing 11 made of a thin resin sheet or film to deform. At that time, the raised part 13 convexly bends at the concavely bent parts 24, respectively, to displace the recess 25, the finger hold 31, and the patch 40 downward toward skin. Since the housing 11 is formed from a thin sheet or film, the raised part 13 easily deforms downward even with a small pressing force, allowing a downward displacement of the recess 25 with ease.

Thus, the patch 40 progresses toward skin with a small force. After contact with skin, the patch 40 progresses vertically together with skin and, in its entirety, is pressed against skin with a uniform force. Since the needles 49 enter perpendicularly into skin, the needles 49 are prevented from bending, damaging, or breaking at the time of puncturing.

Next, when a predetermined pressing force is applied to the finger hold 31, the upper member 32 deforms at its center portion downward by a predetermined amount with respect to the both sides thereof, or the lower member 33 deforms at its center portion upward by a predetermined amount with respect to the both sides thereof, or the upper member 32 and the lower member 33 deform at their respective center portions downward and upward, respectively, with the result that the boss 35 passes through the through-hole 39 of the upper member 32 to protrude by a predetermined length from the top surface thereof, abutting on the finger pressing the finger hold 31. As a result, the boss 35 functions as an indicator so that the user can recognize that a required force is applied to the finger hold 31. Application of the required force to the finger hold 31 allows the needles 49 of the microneedle patch 40 to enter into skin by a predetermined amount. In consequence, the drug carried on the needles 49 can securely be administered to skin.

With the predetermined pressing force being applied, the recess bottom 27 of the raised part 13 bends at the easy-to-deform part 28 so that the undersurface center region 37 and the end regions of the finger hold lower member 33 come into contact with the center region 29 and the end regions (slant surface), respectively, of the recess 25, allowing the microneedles 44 supported on the recess center region to be pressed against skin with a required force. As a result, a sufficient pressure-sensitive adhesive force (which is greater than the pressure-sensitive adhesive force of the double-sided tape 50 to the release treatment layer (release layer) 47) is secured between the patch 40 (particularly, pressure-sensitive adhesive layer 46) and skin.

When the force applied to the finger hold 31 is removed, the housing 11 restores to its pre-deformation shape by its own elasticity, allowing the end regions of the patch 40 adhered to skin to come apart from skin, starting from its edges. Since the undersurface center region 37 and end regions 36 of the finger hold lower member 33 are in contact with the center region 29 and end regions (slant surfaces) 30 of the recess 25, respectively, the ends of the patch 40 lie slant along the end regions 36, with the result that the release force acts on the outer edges of the double-sided tape 50 in a concentrated manner. Consequently, with the patch 40 being adhered to skin, the patch 40 is easily released from the double-sided tape 50 and separates from the housing 11.

Figure 7:
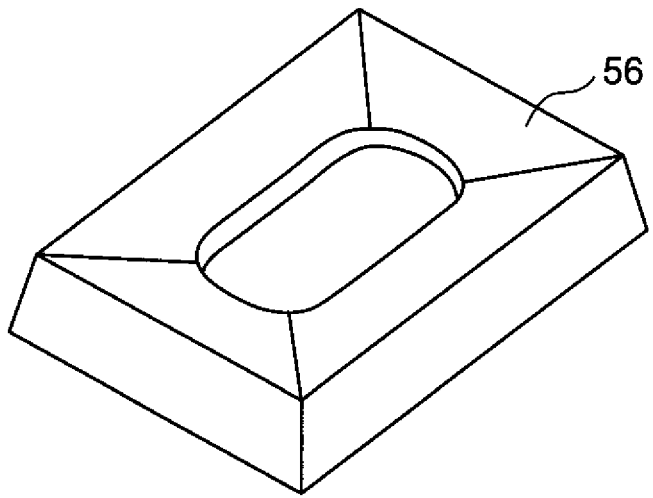
FIG. 7 is a perspective view of a deformation preventing member fitted to a patch storage space of the microneedle patch applicator housing shown in FIG. 1.

As described above, the housing 11 of the applicator 1 is made of a relatively deformable material, and hence it is preferred to prevent the needles 49 from coming into contact with the protective sheet 55 as a result of pre-use deformation of the raised part 13. It is therefore preferred as shown in FIG. 7 to prepare a deformation preventing member 56 having an external shape complementary to the rear shape of the raised part 13 (i.e. the patch storage space 41) and to store the deformation preventing member 56 into the patch storage space 41 before adhesion of the protective sheet 55 or before attachment of the patch 40. For the purpose of preventing deformation, the external shape and material of the deformation preventing member 56 are determined so as to prevent the needles from coming into contact with the protective sheet as a result of a large deformation of the housing 11 even when the housing is subjected to a predetermined force. For the purpose of protecting the needles, the shape of a portion of the deformation preventing member 56 confronting the patch is preferably determined such that a space of predetermined dimensions is formed between the deformation preventing member 56 and the patch. Although the deformation preventing member 56 of this embodiment shown in FIG. 7 has a complementary shape to that of the patch storage space 41, the deformation preventing material may employ any shape as long as the above purposes can be achieved.

Instead of the deformation preventing member 56 or in addition to the deformation preventing member 56, the patch storage space 41 may be hermetically sealed by a protective sheet. The patch storage space may be filled with an inert gas such as nitrogen or a dry gas to replace air therewith. In this case, due to the existence of air or a replacement gas within the hermetically sealed patch storage space, the housing can retain its shape even when it is subjected to an external force, preventing the microneedles from coming into contact with the sheet. A compressed gas may be hermetically enclosed for shape retaining.

Second Embodiment

Figure 8:
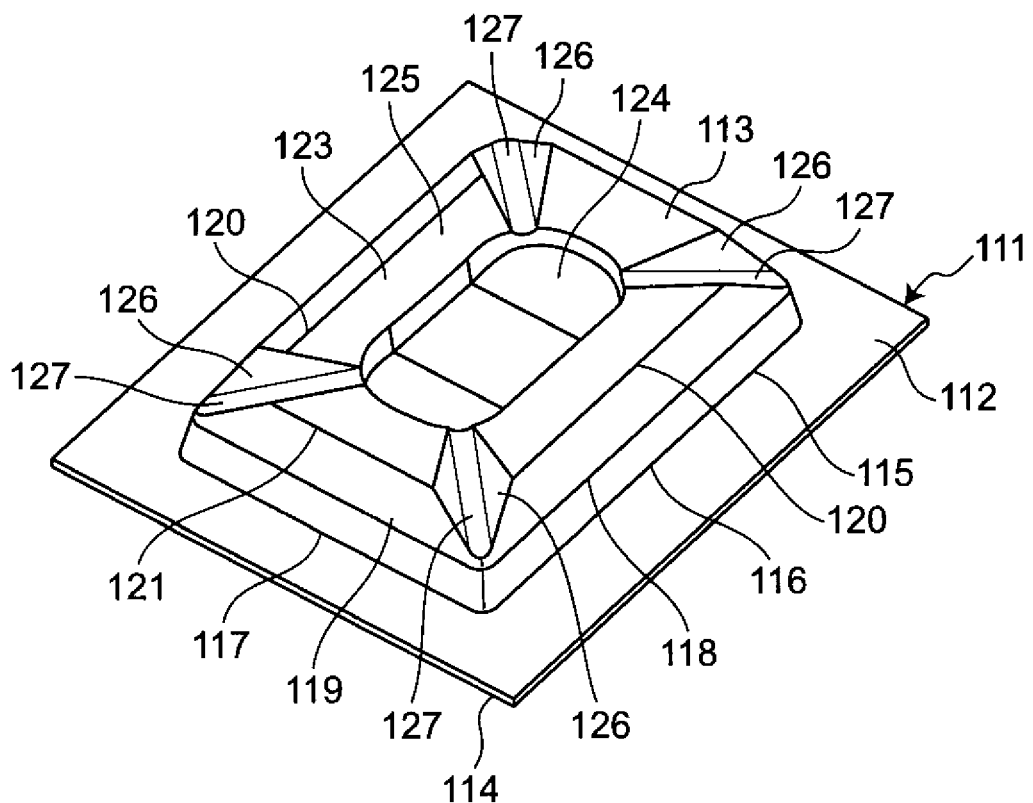
FIG. 8 is a perspective view, from diagonally above, of a microneedle patch applicator and a housing for the same according to a second embodiment.

FIG. 8 shows a housing 111 of an applicator of a second embodiment. Similar to the first embodiment, the housing 111 is formed (e.g. vacuum forming, pressure forming, or press forming) for example from a thin resin sheet or film or molded (e.g. injection molding) from a molten resin injected into a cavity of a mold. A material suitable for forming or molding of the housing is desirably a material having a flexibility and easy to be bent, deformed or restored and can be for example a resin such as polyethylene, polypropylene, polyethylene terephthalate, polystyrene, nylon, acrylic, silicone, or ABS resin. The thicknesses of parts of the housing are properly determined such that a desired deformation described later occurs when the housing 111 is pressed from above with a human finger. For example, in the case of the housing made of polyethylene, polypropylene, or polyethylene terephthalate, the thicknesses of parts are preferably approx. 50 µm to 1 mm, more preferably 100 µm to 500 µm.

The housing 111 comprises a flat plate-like peripheral base part 112 and a raised part 113 that is surround by the peripheral base part 112 and raised upward from the peripheral base part 112. The peripheral base part 112 is surrounded by a substantially rectangular outer edge 114. The raised part 113 has a substantially rectangular contour 115 that is substantially similar to the rectangular outer edge 114 of the peripheral base part 112. In the embodiment, the contour 115 includes a pair of long-side-direction contour parts 116 extending in the long-side direction of the rectangular peripheral base part 112 and a pair of short-side-direction contour parts 117 extending in the short-side direction thereof.

The raised part 113 has a substantially truncated pyramid shape and comprises a long-side-direction side wall 118 and a short-side-direction side wall 119 which extend upward from the long-side-direction contour part 116 and the short-side-direction contour part 117, respectively. The long-side-direction side wall 118 and the short-side-direction side wall 119 may be tilted inward. In the second embodiment, the side walls 118 and 119 each include a lower-stage tilted side wall portion that is slightly tilted and an upper-stage tilted side wall portion that is tilted at a greater tilt angle than that of the lower-stage tilted side wall portion.

A top surface 123 of the raised part 113 includes a peripheral region 125 and a rectangular or track-shaped recess (center region) 124 surrounded by the peripheral region 125, that are bounded by an upper end 120 of the long-side-direction side wall 118 and an upper end 121 of the short-side-direction side wall 119. The peripheral region 125 surrounding the center region 124 of the top surface 123 may be a horizontal surface or a slant surface that is slanted upward or downward, inwardly from the long-side-direction side wall upper end 120 and the short-side-direction side wall upper end 121.

The raised part 113 has at its four corners concavely bent parts 126 extending radially, when viewed from above, from the corners of the raised part 113 toward corners of the center region 124. In the second embodiment, the concavely bent part 126 includes a concave bottom 127 extending horizontally or diagonally upward from the vicinity of a substantial boundary of the upper-stage tilted side wall portion and the lower-stage tilted side wall portion toward the edge of the center region 124.

According to the second embodiment, in the same manner as the first embodiment, the microneedle patch is stored in the patch storage space formed on the back surface of the raised part 113 and is held on the patch support surface that is the back surface of the center region 124. In order to protect the patch stored in the patch storage space, a protective sheet of a size enough to close the opening of the patch storage space may be affixed to the undersurface of the housing 1 (see FIG. 2) and the protective sheet may have an easy peel feature so as to allow easy manual opening. Furthermore, the raised part 113 may have on its center region 124 the finger hold described in the first embodiment.

According to the applicator and housing of the second embodiment configured in this manner, when the applicator storing the patch is placed on skin and the center region 124 of the housing or the finger hold disposed thereon is pressed, the concavely bent part 126 is concavely bent around the concave bottom 127, allowing the raised part 113 of the housing to deform downward. At this time, since the housing 111 is made of a thin sheet or film, the raised part 113 easily deforms downward even with a small pressing force. The patch progresses perpendicularly more deeply toward skin with a small force and, in its entirety, is pressed against skin with a uniform force. Since the needles enter perpendicularly into skin, the needles are prevented from bending, damaging, or breaking at the time of puncturing.

In the second embodiment, similarly to the first embodiment, the deformation preventing member may be disposed in the patch storage space; the patch storage space may be hermetically sealed by the protective sheet; and/or a compressed gas may be hermetically filled in the patch storage space completely sealed by the protective sheet. A moisture absorbent or an oxygen absorbent may be filled in the interior of the housing; the housing itself may be made of a moisture absorbing material; or it may be made of an oxygen absorbing material.

Third Embodiment

Figure 9:
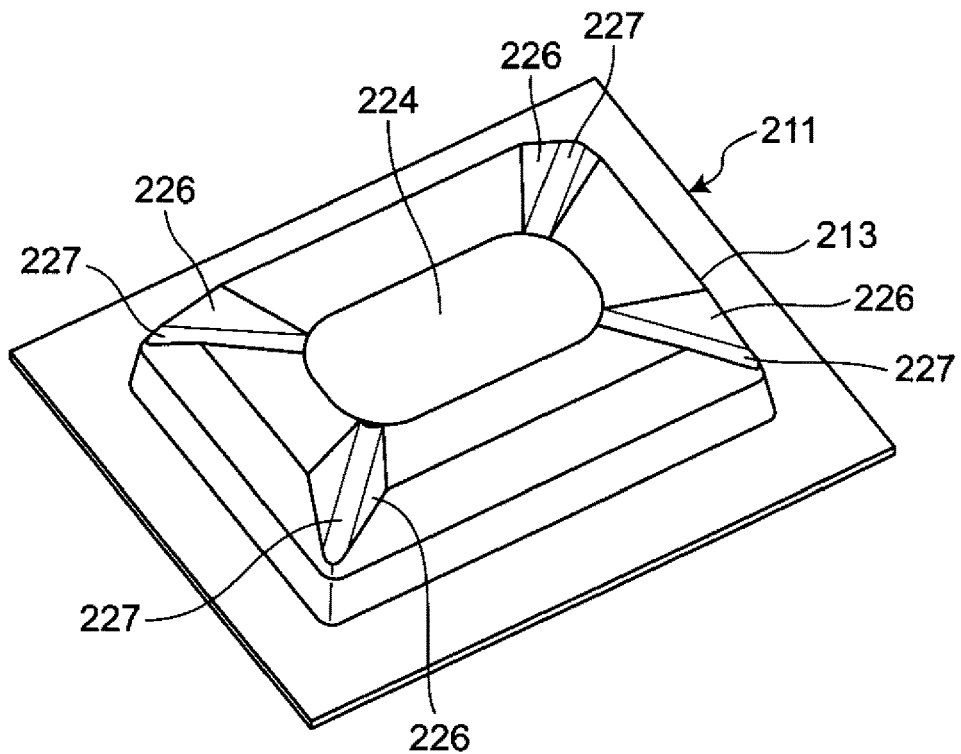
FIG. 9 is a perspective view, from diagonally above, of a microneedle patch applicator housing according to a third embodiment.

FIG. 9 shows a housing 211 of a third embodiment. The third embodiment is a variant of the second embodiment, in which a top surface center region 224 of a raised part 213 is planar without a recess. The other configurations are the same as those of the second embodiment.

According to the third embodiment configured in this manner, similarly to the first and second embodiments, when the applicator storing the patch is placed on skin and a center region 224 of the housing or the finger hold disposed thereon is pressed, a concavely bent part 226 is concavely bent around a concave bottom 227, allowing a raised part 213 of the housing to deform downward. At this time, since the housing is made of a thin sheet or film, the raised part 213 easily deforms downward even with a small pressing force. The patch progresses perpendicularly more deeply while pressing skin with a small force and, in its entirety, is pressed against skin with a uniform force. Since the needles enter perpendicularly into skin, the needles are prevented from bending, damaging, or breaking at the time of puncturing.

Fourth Embodiment

Figure 10:
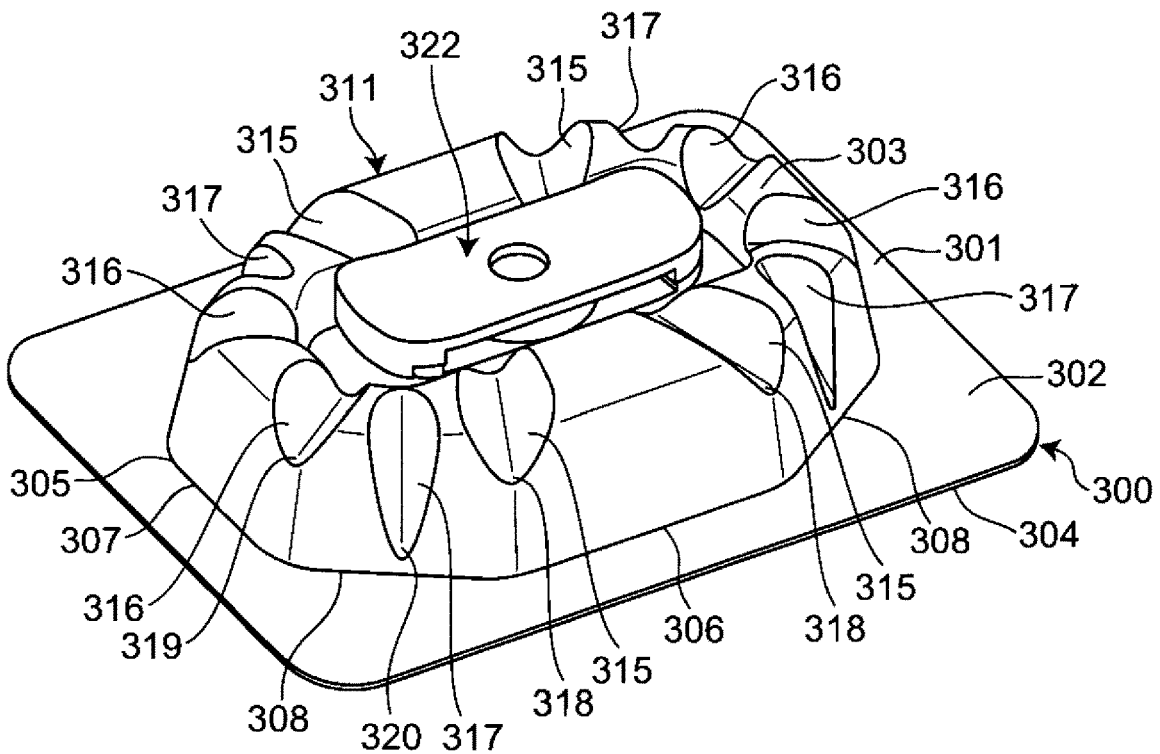
FIG. 10 is a perspective view, from diagonally above, of a microneedle patch applicator and a housing for the same according to a fourth embodiment.
Figure 11:
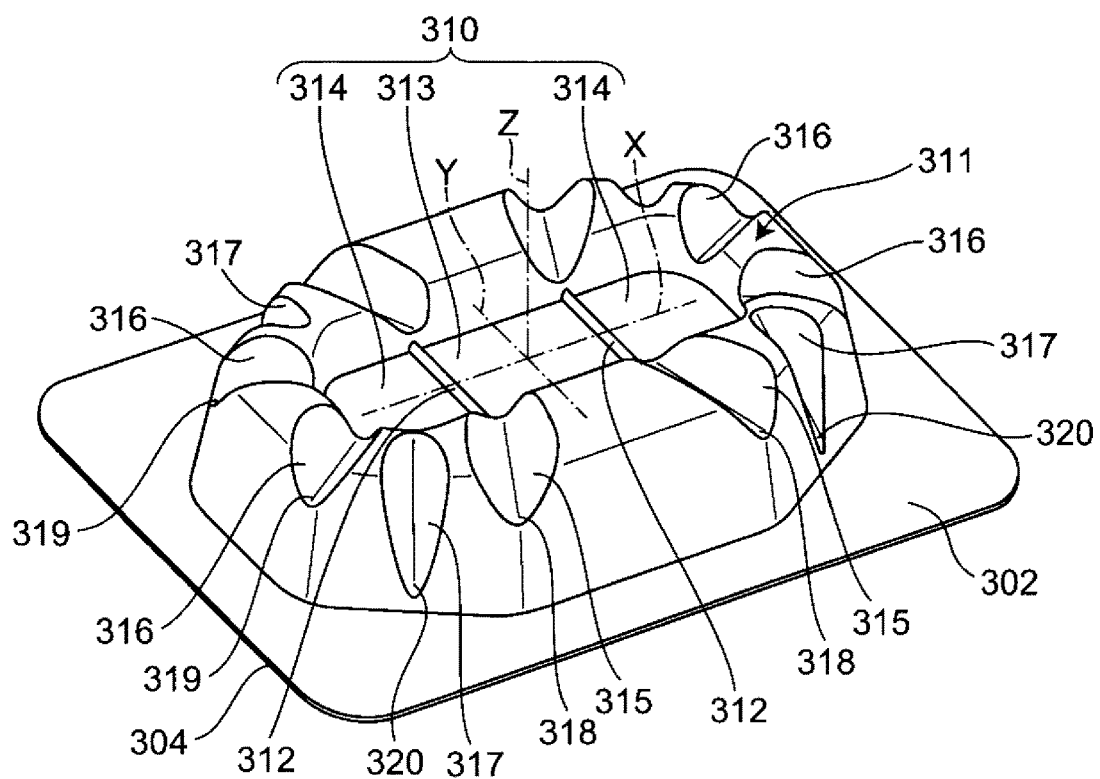
FIG. 11 is a perspective view, from diagonally above, of the housing shown in FIG. 10.
Figure 12:
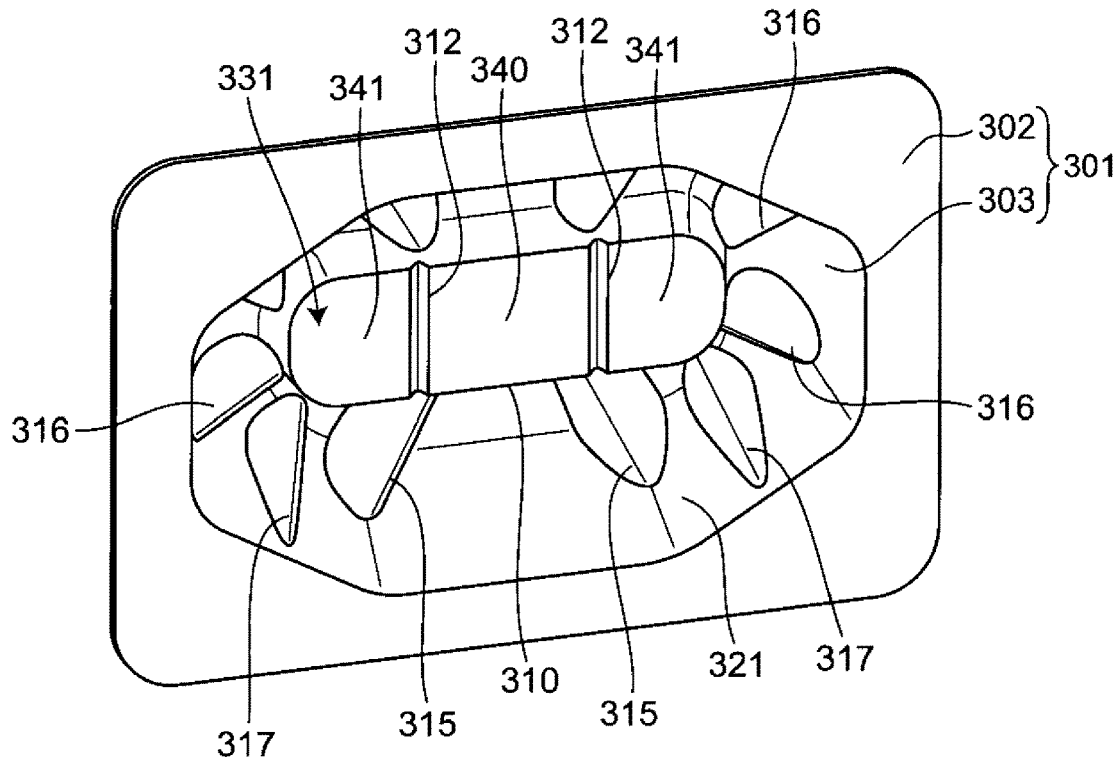
FIG. 12 is a perspective view, from diagonally below, of the housing shown in FIG. 10.

FIG. 10 shows a microneedle patch applicator 300 according to a fourth embodiment, with FIGS. 11 and 12 showing a housing 301 for the applicator.

The applicator 300 comprises the housing 301 holding a microneedle patch 330 that will be described later.

The housing 301 is formed (e.g. vacuum forming, pressure forming, or press forming) for example from a thin resin sheet or film or molded (e.g. injection molding) from a molten resin injected into a cavity of a mold and has an external shape shown. Examples of a material suitable for forming or molding of the housing include polyethylene, polypropylene, polyethylene terephthalate, polystyrene, nylon, acrylic, silicone, and ABS resins. The thicknesses of parts of the housing are properly determined such that a desired deformation described later occurs when the housing 301 is pressed from above with a human finger. For example, in the case of the housing made of polyethylene, polypropylene, or polyethylene terephthalate, the thicknesses of parts are preferably approx. 50 μm to 1 mm, more preferably 100 μm to 500 μm.

The housing 301 comprises a flat plate-like peripheral base part 302 and a raised part 303 that is surround by the peripheral base part 302 and raised upward (in z-axis direction of FIG. 11) from the peripheral base part 302. The peripheral base part 302 is surrounded by a substantially rectangular outer edge 304. The raised part 303 has a substantially octagonal contour 305 when viewed from above. The contour 305 includes a pair of long-side-direction contour parts 306 extending in the long-side direction (x-axis direction of FIG. 11) of the peripheral base part 302, a pair of short-side-direction contour parts 307 extending in the short-side direction (y-axis direction of FIG. 11) thereof, and four diagonal contour parts 308 each intersecting the long-side direction and the short-side direction at a predetermined angle.

The raised part 303 comprises a caldera basin-like flat recess 310 at a center thereof and a somma-like ridge 311 extending along the outer circumference of the recess 310 so as to encompass the recess 310. The bottom of the recess 310 lies at a position enough higher than that of the peripheral base part 302 so that, when the housing 301 is placed on skin, a sufficient space is secured between skin and the back surface (which is a surface supporting the microneedle patch 330 (see FIG. 13) as will be described later) of the recess 310.

The recess 310 has a track-shaped contour having a pair of parallel long-side-direction edges and substantially semi-arcuate edges joining ends thereof. In the embodiment, the recess 310 includes a pair of easy-to-deform parts 312 extending straight in the short-side direction, at positions apart a predetermined distance in the long-side direction (x-axis direction) from a center position (position at which x-axis and y-axis intersect) in the long-side direction. In this embodiment, the easy-to-deform parts 312 are formed with their respective portions being curved upward so that end regions 314 lying on both sides of a center region 313 defined by the easy-to-deform parts 312 are easily bent upward relative to the center regions 313 around the easy-to-deform parts 312.

The ridge 311 includes a plurality of concavely bent parts radially crossing the ridge 311 from its inside to outside. In the embodiment, the ridge 311 includes 12 concavely bent parts 315, 316, and 317. The 12 concavely bent parts 315, 316, and 317 are each formed symmetrically with respect to a vertical axis (z-axis) extending through the center of the recess 310, a long axis (x-axis), and a short axis (y-axis). For example, at boundaries between each of the long-side-direction contour parts 306 and two diagonal contour parts 308 adjacent thereto, two first concavely bent parts 315 are radially arranged in such a manner that the distance between the concavely bent parts increases gradually from the inside to the outside. At boundaries between each of the short-side-direction contour parts 307 and two diagonal contour parts 308 adjacent thereto, two second concavely bent parts 316 are radially arranged in such a manner that the distance between the concavely bent parts increases gradually from the inside to the outside. A single third concavely bent part 317 is formed at the center of each of the diagonal contour parts 308.

A concave bottom 318 of the first concavely bent part 315, a concave bottom 319 of the second concavely bent part 316, and a concave bottom 320 of the third concavely bent part 317 are horizontal concave bottoms extending horizontally parallel to the peripheral base part 302 or are slant concave bottoms slanting toward the peripheral base part below.

Preferably, the concavely bent part is disposed at a plurality of locations where a deformation may occur in a housing not having the concavely bent part when a force is applied via a finger hold (pressed portion) 322 to the housing not having the concavely bent part. This allows even a weak force to deform the housing into a desired shape, so that the housing can achieve a stable deformation.

The concavely bent part is preferably of a shape to facilitate the deformation of the housing. It is therefore preferred to change the angle of the concave bottom, the shape, size, etc. of the concavely bent part so as to fit the shape, etc. of the raised part. In consequence, the housing can be deformed into a desired shape even with a small force and can achieve a stable deformation.

Figure 13:
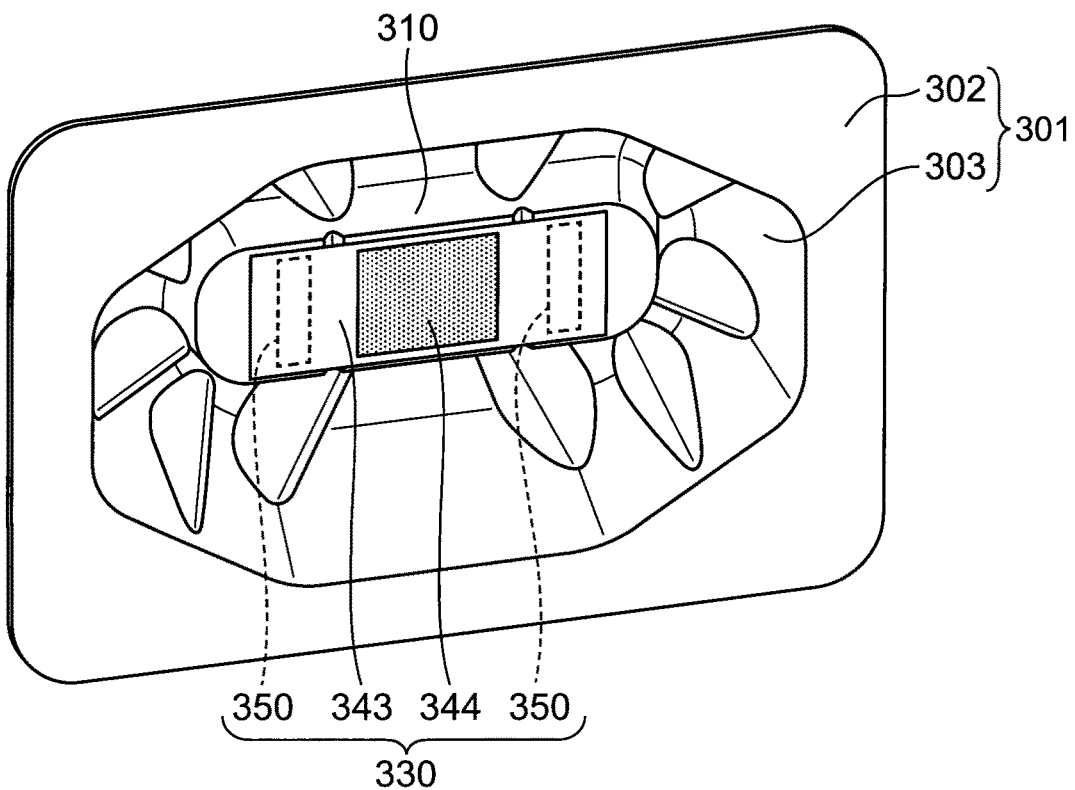
FIG. 13 is a perspective view, from diagonally below, of the housing of FIG. 10 to which the microneedle patch is attached.

The housing 311 is formed by molding a thin sheet or film as described above and, at the back of the raised part 303, as shown in FIG. 12, comprises a microneedle patch storage space (recess) 321 of a shape corresponding to that of the raised part 303. The recess 321 has on its back surface a patch support surface 331. The patch support surface 331 includes a center region 340 and end regions 341 corresponding to the back side of the center region 313 and the end regions 314 of the recess 321. As shown in FIG. 13, the patch 330 is disposed on the patch support surface 331, with a microneedle array 344 being supported on the center region 340, a double-sided tape 350 being carried on the both end regions 341. The double-sided tape 350 may be replaced by an adhesive.

Figure 14:
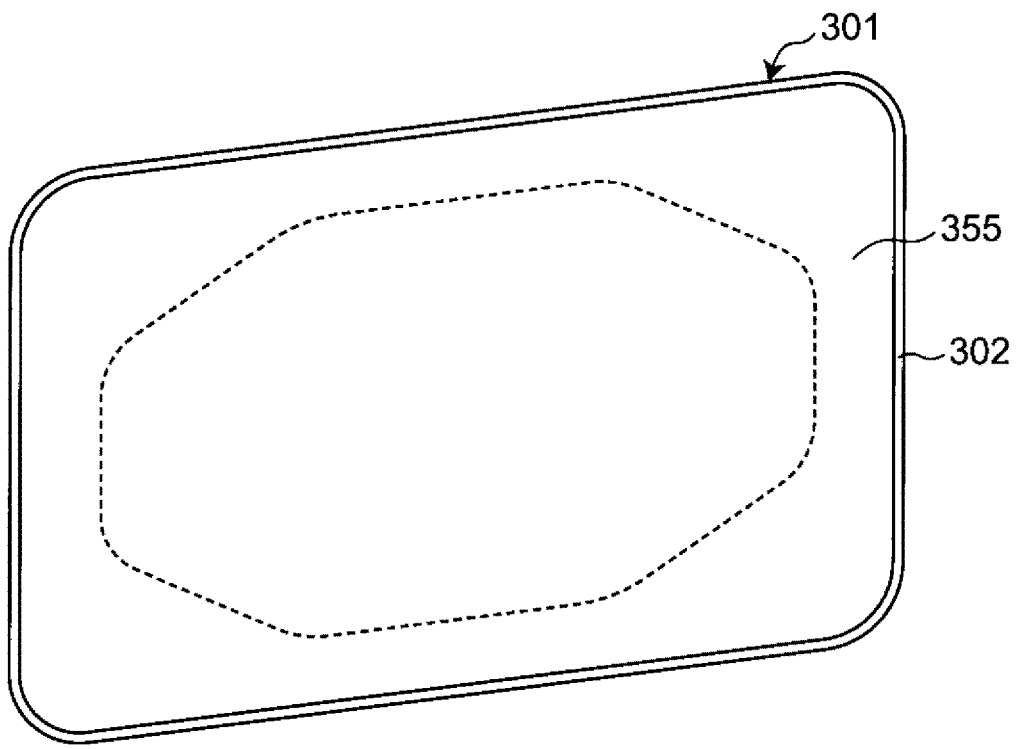
FIG. 14 is a perspective view, from diagonally below, of the housing of FIG. 10 having a bottom to which a protective seal is affixed.
Figure 15:
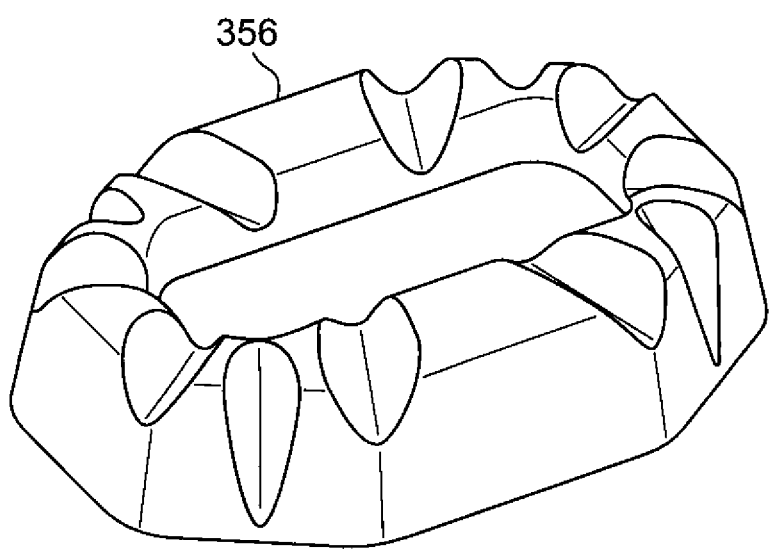
FIG. 15 is a perspective view of a deformation preventing member fitted to the housing shown in FIG. 10.

Otherwise, configurations of the finger hold 322 (see FIG. 10), the microneedle patch 330 (see FIG. 13), a protective sheet 355 (see FIG. 14), and a deformation preventing member 356 (see FIG. 15) are the same as in the first to third embodiments.

According to the applicator 300 and the housing 301 configured in this manner, because the concave bottom 320 of the third concavely bent part 317 extends diagonally downward from the inside toward the outside, the resistance force of the housing 301 against an inward deformation (which, at the same time, induces a vertical deformation toward the base) of the raised part 303 becomes reduced. Hence, the raised part 303 causes the patch 330 to advance vertically toward skin, while inwardly deforming in such a manner that its entirety contracts. As a result, the patch 330 advances vertically more deeply against skin with a small force and is, in its entirety, pressed against skin with a uniform force. Since the needles enter vertically into skin, the needles cannot be bent, damaged, or broken at the time of puncturing.

Fifth Embodiment

Figure 16:
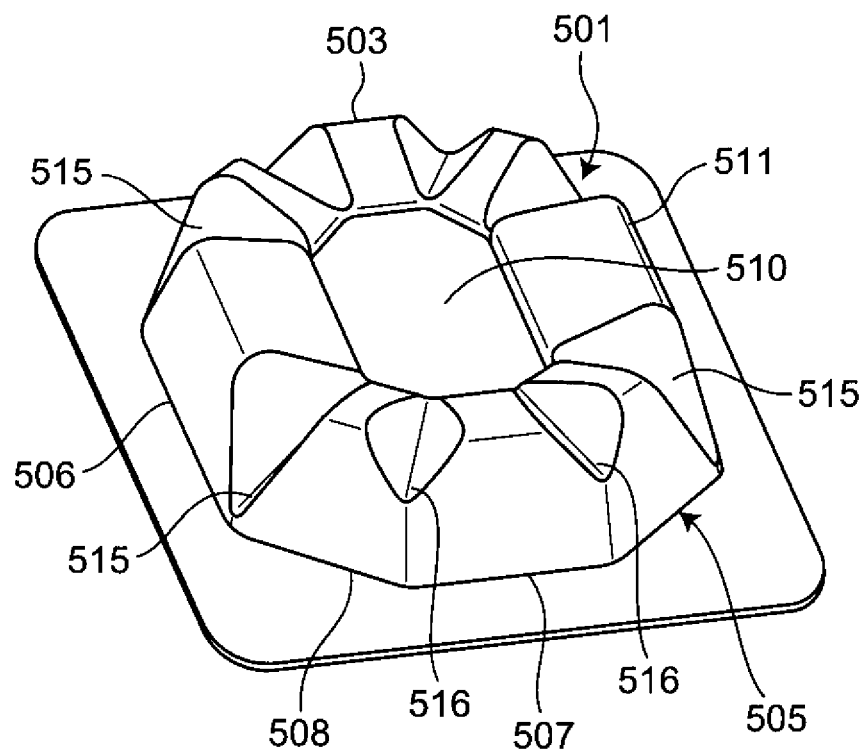
FIG. 16A is an upper perspective view of a microneedle patch applicator and a housing for the same according to a fifth embodiment.
FIG. 16B is a lower perspective view of the microneedle patch applicator and the housing for the same according to a fifth embodiment.
Figure 16:
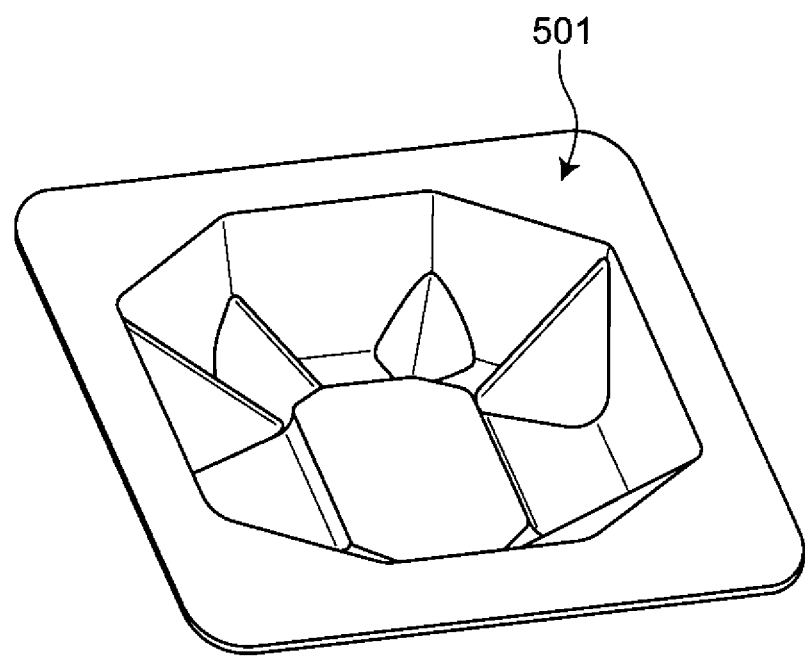

FIG. 16 shows a housing 501 of an applicator according to a fifth embodiment. In the housing 501, a raised part 503 is of a substantially octagonal shape when viewed from above, with its contour 505 including a long-side-direction contour part 506 extending in the long-side direction, a short-side-direction contour part 507 extending in the short-side direction, and a diagonal contour part 508. A ridge 511 has concavely bent parts 515 and 516 formed at their respective locations corresponding to boundaries of the long-side-direction contour part 506 in the long-side direction, the short-side-direction contour part 507 in the short-side direction, and the diagonal contour part 508. A concave bottom of the concavely bent part 515 is sloped downward toward the peripheral base part. A concave bottom of the concavely bent part 516 may be sloped downward toward the peripheral base part or may be horizontal parallel to the peripheral base part.

In the fifth embodiment configured in this manner, because the deformation is made allowing the concave bottom of the concavely bent part 515 to be displaced in the inside direction orthogonal thereto, the vertical progression properties of the recess 510 and the patch can be enhanced. As a result, the patch advances vertically against skin with a small force and is, in its entirety, pressed against skin with a uniform force. Since the needles enter vertically into skin, the needles cannot be bent, damaged, or broken at the time of puncturing.

Sixth Embodiment

Figure 17:
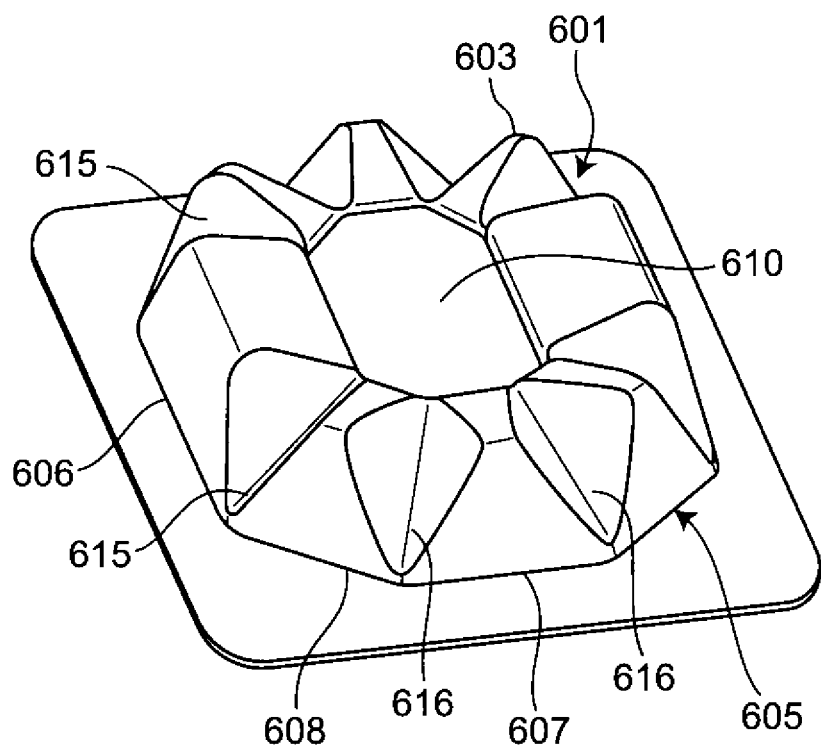
FIG. 17A is an upper perspective view of a microneedle patch applicator and a housing for the same according to a sixth embodiment.
FIG. 17B is a lower perspective view of the microneedle patch applicator and the housing for the same according to a sixth embodiment.
Figure 17:
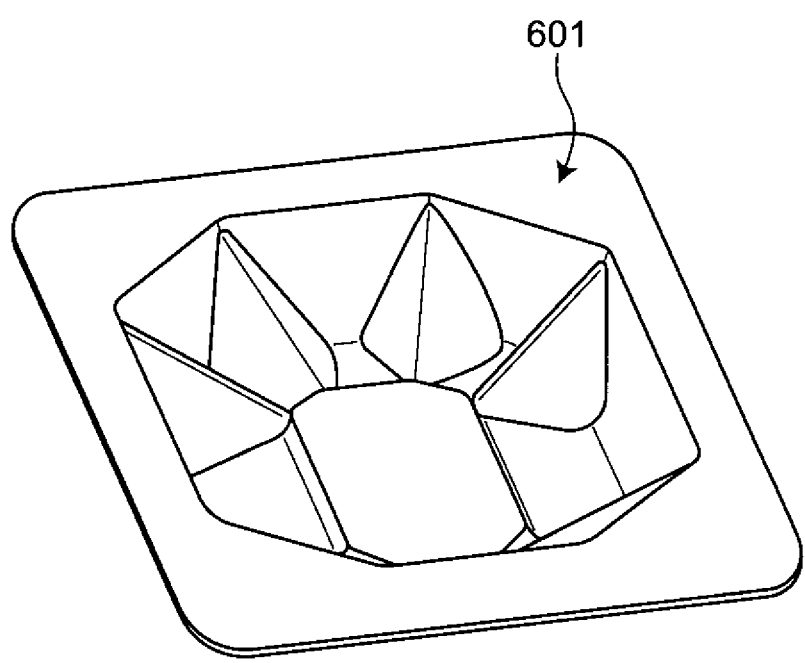

FIG. 17 shows a housing 601 of an applicator according to a sixth embodiment. In the housing 601, a raised part 603 is of a substantially octagonal shape when viewed from above, with its contour 605 including a long-side-direction contour part 606 extending in the long-side direction, a short-side-direction contour part 607 extending in the short-side direction, and a diagonal contour part 608, with concavely bent parts 615 and 616 being formed at boundaries of the adjacent contour parts 605, 606, and 607. Concave bottoms of the concavely bent parts 615 and 616 are sloped downward from the inside toward the outside.

In the sixth embodiment configured in this manner, directions of downward deformation of the concavely bent parts 615 and 616 having the sloped concave bottoms are symmetric with respect to a vertical plane containing the long axis of the recess 610 and to a vertical plane containing the short axis thereof and are directed diagonally inside, allowing the recess 610 and the patch carried on the back surface thereof to advance vertically against the recess 610. As a result, the patch advances vertically and more deeply against skin and is, in its entirety, pressed against skin with a uniform force. Since the needles enter vertically into skin, the needles cannot be bent, damaged, or broken at the time of puncturing.

In this embodiment, the slope angle of the concave bottoms of the concavely bent parts 615 lying on both sides of the long-side-direction contour part 606 may be equal to the slope angle of the concave bottoms of the concavely bent parts 616 lying on both sides of the short-side-direction contour part 607, or one may be greater than the other.

Seventh Embodiment

Figure 18:
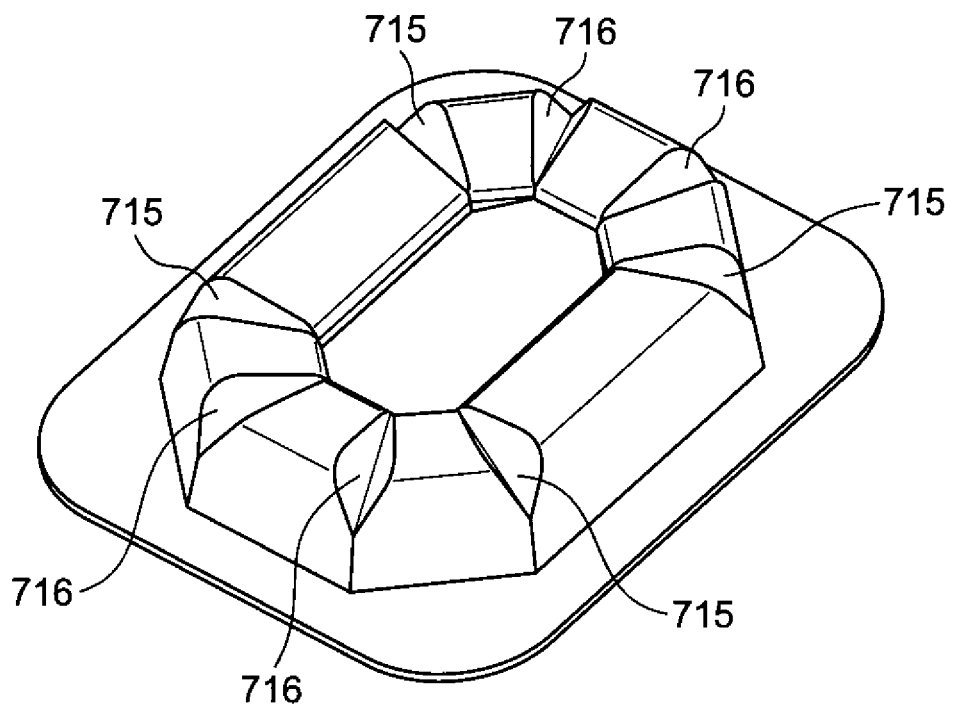
FIG. 18 is a perspective view, from diagonally above, of a microneedle patch applicator and a housing for the same according to a seventh embodiment.

Although in the sixth embodiment the concave bottoms of all the concavely bent parts are sloped downward from the inside of the raised part toward the outside thereof, the concave bottoms of all the concavely bent parts 715 and 716 may be directed horizontally parallel to the peripheral base part as shown in FIG. 18, or one of the concavely bent parts 715 and 718 may be sloped with the other being directed horizontally.

Eighth Embodiment

Figure 19:
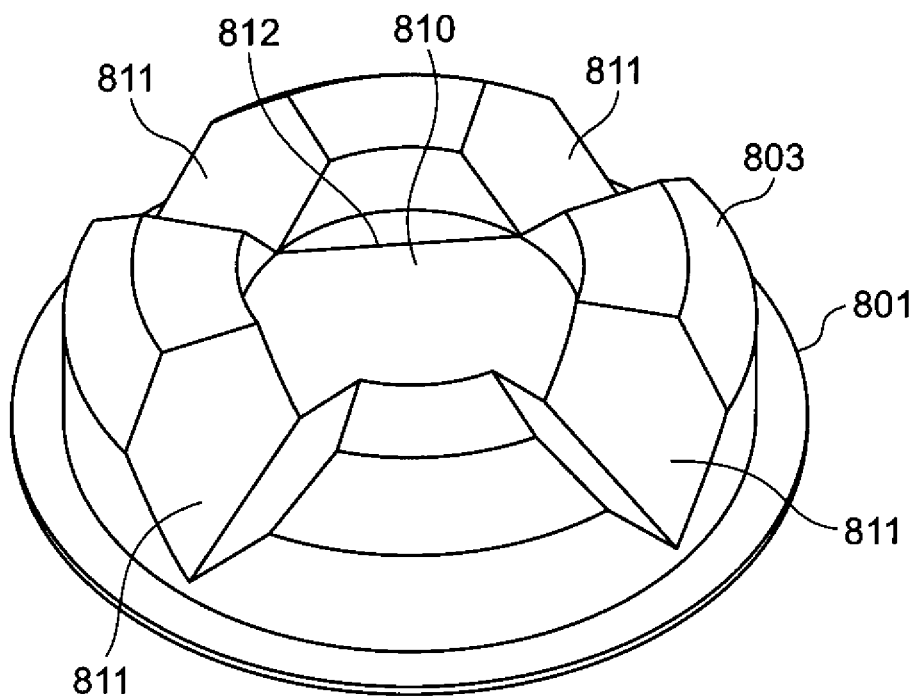
FIG. 19A is an upper perspective view of a microneedle patch applicator and a housing for the same according to an eighth embodiment.
FIG. 19B is a lower perspective view, from diagonally above, of the microneedle patch applicator and the housing for the same according to an eighth embodiment.
Figure 19:
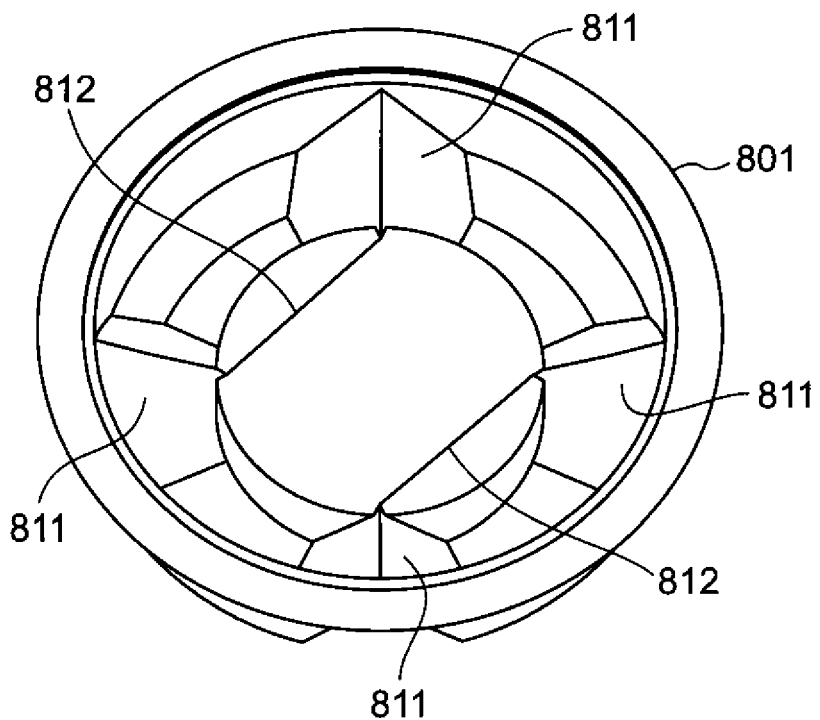
Figure 20:
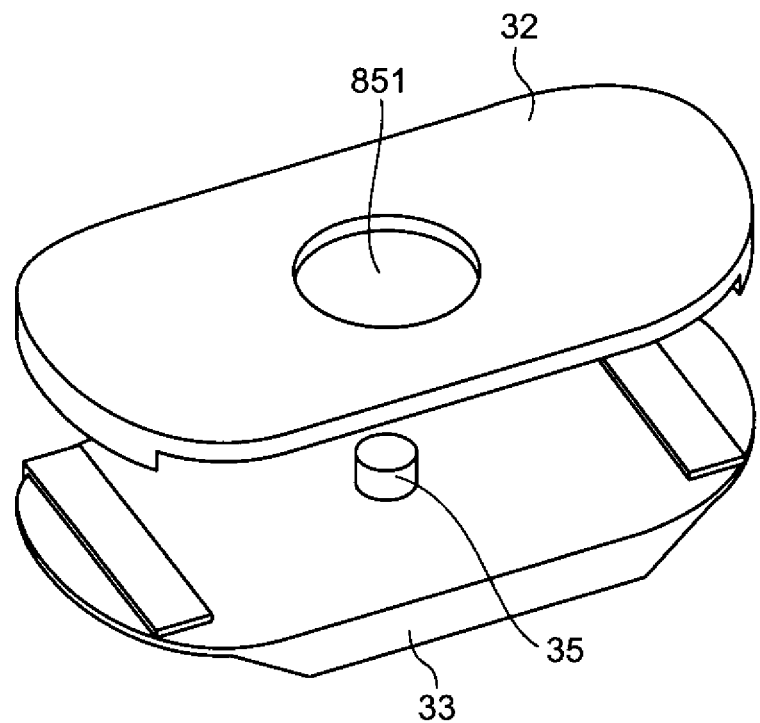
FIG. 20 is an exploded perspective view showing a finger hold of another mode.

Although in the above embodiments the raised part of the housing has a polygonal contour, a raised part 803 may have a circular contour as shown in FIG. 19. In this embodiment, the raised part 803 of a housing 801 may have a plurality of concavely bent parts 811 arranged circumferentially equiangularly and extending radially from the center of a recess 810 or may have a plurality of concavely bent parts arranged rotationally symmetrically on a vertical axis extending through the center of the raised part. It is preferred also in the housing of the eighth embodiment, similarly to the above embodiments, that the recess 810 have at least two easy-to-deform parts 812 extending in parallel.

Variants

In the above embodiments, the planar shape of the housing raised part is not limitative and may be a polygonal shape such as quadrangle, pentagon, and hexagon or may be a circle, ellipse, or a track shape. It is preferred in all the modes the concavely bent part whose concave bottom is sloped and the concavely bent part having a sloped concave bottom are symmetrical with respect to a vertical plane containing the long axis or the short axis of the raised part. In the case of polygons such as pentagon having an odd number of sides, the concavely bent parts having a sloped concave bottom are preferably arranged circumferentially equiangularly around the vertical axis. Although in the case of the circular raised part the long axis and the short axis cannot be distinguished from each other, the concavely bent parts whose concave bottoms are sloped may be arranged symmetrically with respect to at least one of two axes (orthogonal horizontal axes X and Y) orthogonal to the center axis (Z-axis in the vertical direction) or may be arranged centrosymmetrically with respect to the center axis.

Similarly, the shapes of the recess and corresponding finger hold are not limited to the track shape and may be any one of ellipse, circle, quadrangle, and the other polygons.

The ridge need not continuously be disposed around the recess and may be discontinuous.

Although in the above description the patch is pressed via the finger hold against skin, the recess may directly be pressed by a finger without using the finger hold.

The raised part need not necessarily have the recess, and the top of the raised part may be a flat surface not having the recess. In this case, the concavely bent parts are formed on the outer periphery of the raised part. The number of the concavely bent parts and the slope angle of the concave bottom are properly selected so as to ensure the needles' vertical puncturing properties.

The finger hold need not have the through-hole in its upper member, correspondingly to the boss on the lower member, and the upper member 32 may have a thinned portion 851 at a location confronting the boss 35 on the lower member 33 so that when a necessary force is applied to the finger hold, the boss 35 deforms or breaks the thinned portion 851. In this case, the thinned portion 851 functions as an indicator informing the operator that a predetermined pressing force has been applied to the finger hold.

The indicator informing the operator that a predetermined pressing force has been applied to the finger hold may be configured for example such that when a predetermined pressing force is applied to the finger hold, specific feature portions formed on both the upper member and the lower member come into contact with each other or move away from each other so that the specific feature portion disposed on one of the upper member and the lower member is broken to issue a sound (contact sound or breakdown sound). Specifically, one of the upper member and the lower member may be provided with an aperture or the like, with the other being provided with a projection that snap-fits into the aperture so that those fitting-in brings about a click feeling or issues a sound. Alternatively, configuration may be such that metal or resin in the form of a dome spring for example is deformed that is a circular plate having a slightly downward convex curved surface so that e.g. when the circular plate is pressed at its center portion from above toward below, the upward convex curved surface is warped into a concave curved surface to produce a sound or vibration at that time.

Ninth Embodiment

Figure 21:
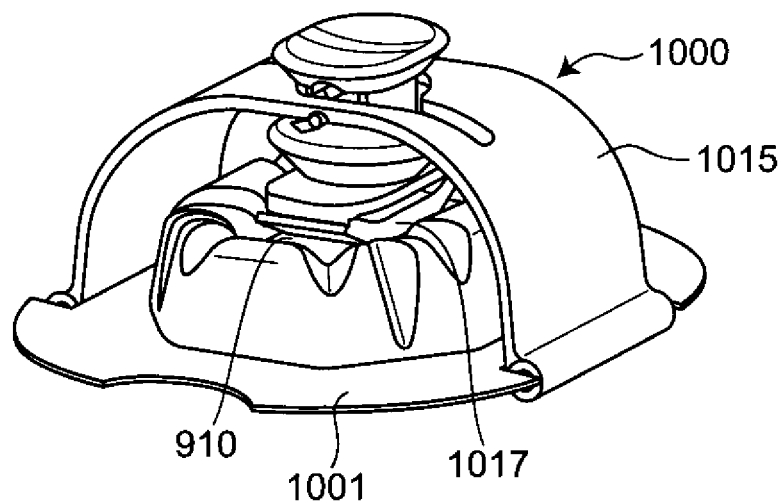
FIG. 21 is a perspective view of a microneedle patch applicator according to a ninth embodiment.

FIG. 21 shows an applicator 1000 of a ninth embodiment. The applicator 1000 comprises a housing 1001 and a pressing mechanism 1015.

Figure 22:
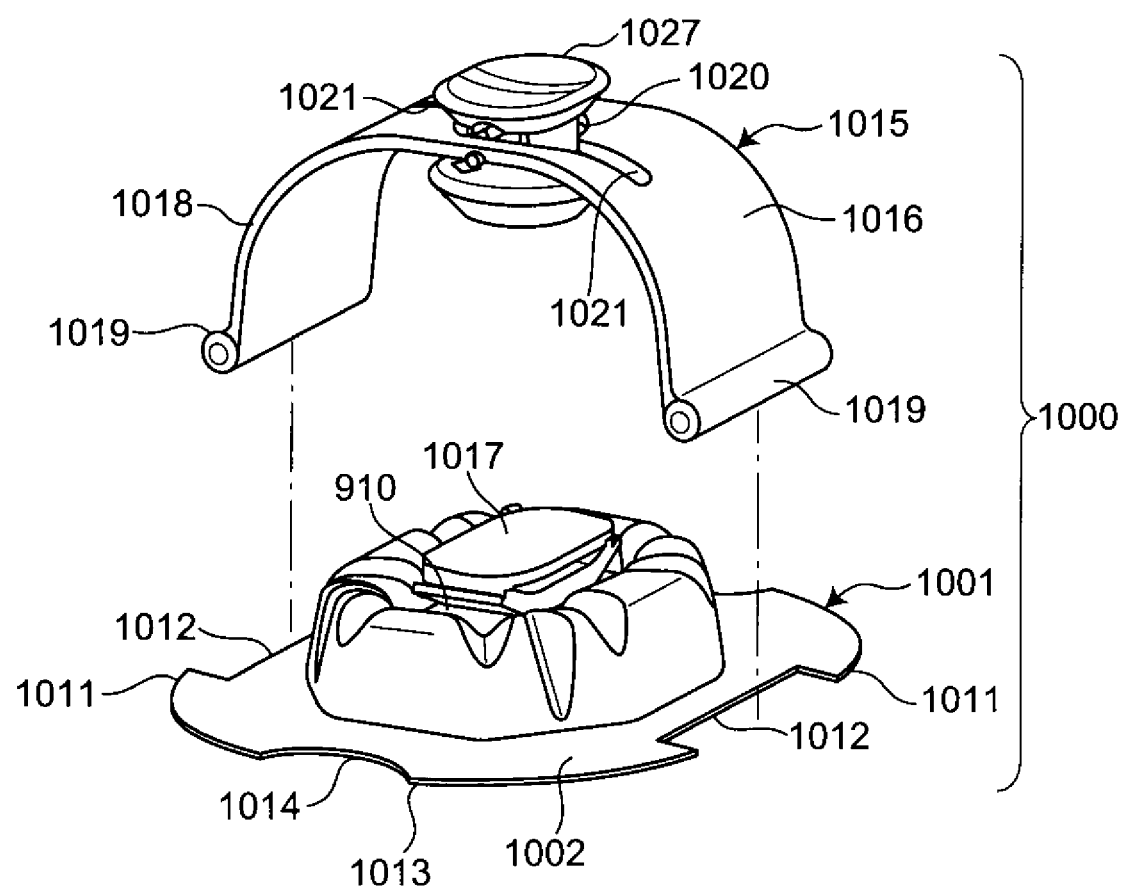
FIG. 22 is a partially exploded perspective view of the microneedle patch applicator according to the ninth embodiment shown in FIG. 21.

As shown in FIG. 22, similarly to the above embodiments, the housing 1001 comprises a peripheral base part 1002. The peripheral base part 1002 has in its long-side-direction edges 1011 a notch 1012 in the shape of a bracket for example. The peripheral base part 1002 has in its width-side edge 1013 a notch 1014 in the shape of an arch for example. Other than the above, the housing 1001 is substantially the same as the housing 301 of the fourth embodiment. Accordingly, the housing 1001 will not be again described. In the following description, parts of the housing 1001 are appropriately designated at reference numerals of 900 s that are obtained by adding 600 to reference numerals imparted to corresponding parts of the housing of the fourth embodiment.

The pressing mechanism 1015 generally comprises an upper structure 1016 and a lower structure 1017. The upper structure 1016 comprises a substantially inverted-U-shaped or substantially inverted-arch-shaped elastic expansion part 1018. The elastic expansion part 1018 is made of e.g. a synthetic resin having an elasticity. Accordingly, when the elastic expansion part 1018 is subjected at its center portion to a force from above, the elastic expansion part 1018 can deform such that both end portions 1019 thereof move outward apart from each other. In the embodiment, the both end portions 1019 of the elastic expansion part 1018 are formed into a substantially cylindrical shape. Ina free state, the interval between the left and right end portions 1019 is equal to or slightly greater than the distance between a pair of bracket-shaped notches 1012 formed in the long-side-direction edges 1011 of the housing 1001.

The elastic extension part 1018 has at its center region a substantially quadrangular opening 1020 extending through a top surface and an undersurface thereof. The top surface of the elastic expansion part 1018 includes a pair of grooves 1021 extending straight outward from diagonally confronting corners of the opening 1020 toward the both end portions 1019.

Figure 23:
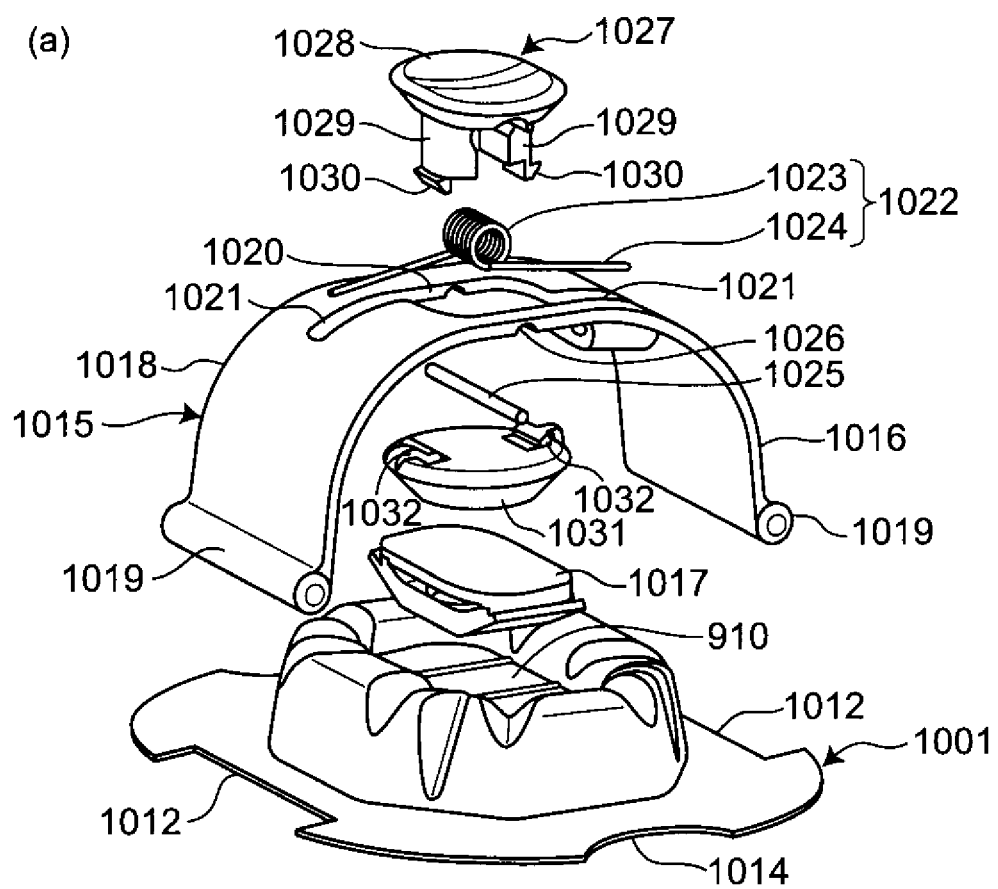
FIG. 23A is an exploded perspective view (FIG. 23(A)) of the microneedle patch applicator according to the ninth embodiment shown in FIG. 21.
FIG. 23B is a front view of a torsion spring assembled in the microneedle patch applicator shown in FIG. 23A.
Figure 23:
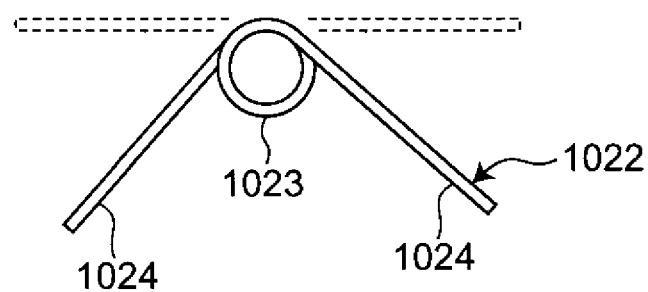

As shown in FIG. 23, a torsion spring 1022 is stored in the opening 1020 and the grooves 1021. The torsion spring 1022 includes a winding portion 1023 of a wound wire and a pair of arm portions 1024 extending straight from both ends of the winding portion 1023. The thus configured torsion spring 1022 is retained via a pin 1025 on the elastic expansion part 1018, with the winding portion 1023 being stored in the opening 1020, with the arm portions 1024 being stored in the grooves 1021. The pin 1025 engages with the center undersurface of the elastic expansion part 1018 so that the winding portion 1023 is retained in the opening 1020, with the arms of the torsion spring 1022 being contracted from a position indicated by a solid line in FIG. 23(*b*) to a position indicated by a broken line, whereby the elastic expansion part 1018 is biased by the arm portions 1024 such that its both end portions 1019 come closer to each other.

In the embodiment, the elastic expansion part 1018 has at its undersurface center a groove 1026 extending in the width direction in order to position the pin 1025, with the pin 1025 being stored in the groove 1026.

A finger hold 1027 is assembled on the elastic expansion part 1018. The finger hold 1027 includes an upper portion 1028 against which the user presses his/her finger (e.g. thumb) and a pair of legs 1029 extending downward from the undersurface of the upper portion 1028. Each of the legs 1029 has at its lower end an engaging portion 1030. The thus configured finger hold 1027 is assembled on the elastic expansion part 1018, with the winding portion 1023 of the torsion spring 1022 being positioned between the legs 1029, with the legs 1029 being inserted into the opening 1020 from above to below.

The lower end engaging portions 1030 of the legs 1029 projecting downward from the opening 1020 are engaged with and retained by a coupling member 1031. The coupling member 1031 is a substantially circular member and includes, at its top surface symmetrical locations, engaged portions 1032 of a shape corresponding to that of the lower end engaging portion 1030, with the lower end engaging portions 1030 of the legs 1029 being inserted into the engaged portions 1032 so that the finger hold 1027 is coupled to the coupling member 1031.

Figure 24:
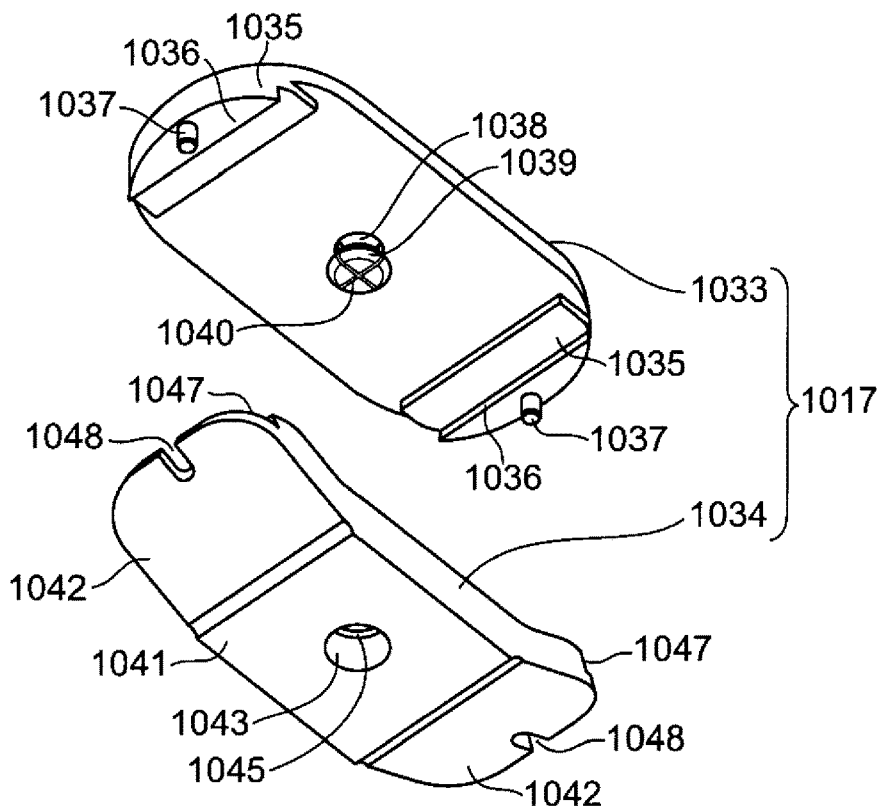
FIG. 24A is a lower, exploded perspective view of a lower structure assembled in the microneedle patch applicator according to the ninth embodiment of FIG. 21.
FIG. 24B is an upper perspective view of the lower structure in perspective view.
FIG. 24C is a bottom view of the lower structure.
Figure 24:
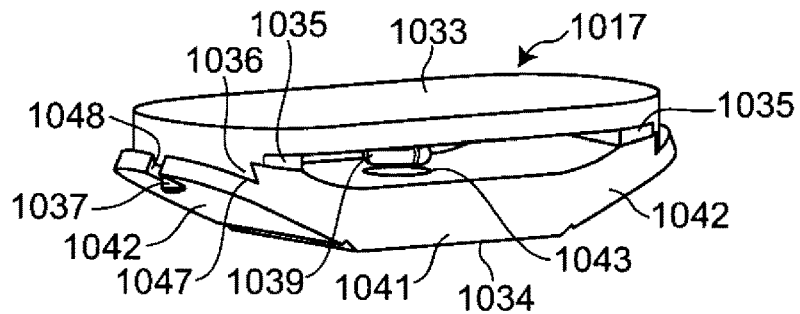
Figure 24:
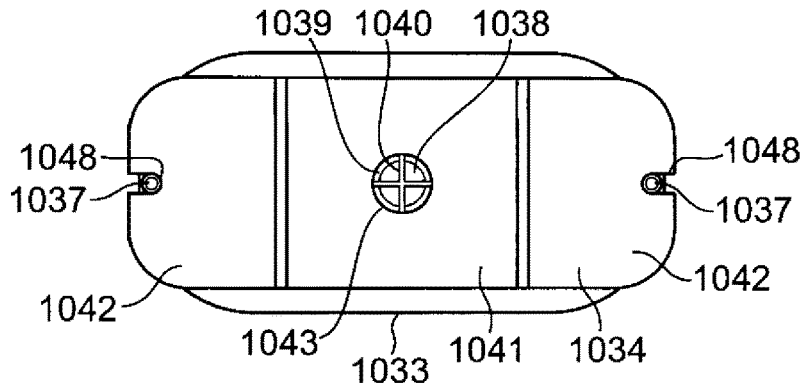

The lower structure 1017 includes, as shown in FIG. 24, an upper member 1033 and a lower member 1034. When viewed from above, the upper member 1033 and the lower member 1034, particularly the lower member 1034 is of a track shape substantially equal in size to a recess 910 of the housing 1001. The undersurface of the upper member 1033 includes, at its both ends in the longitudinal direction, a platform 1035 projecting downward. The platforms 1035 have, at both end sides in the longitudinal direction, their respective hook portions 1036 extending in the width direction, the hook portions 1036 each having at its center edge a projection 1037 projecting downward. The upper member 1033 has a cylindrical boss 1038 on the undersurface at the center. The cylindrical boss 1038 has at its lower end a diameter slightly larger than that of the other portions. The cylindrical boss 1038 includes a vertical cross groove extending, in the long-side direction and the short-side direction of the upper member 1033, along the center axis upward from the lower end surface, whereby the lower end 1039 can deform so that its outer diameter reduces when a force is applied from the periphery.

The lower member 103 generally comprises a center plate portion 1041 and a slant plate portion 1042 extending diagonally upward from both ends of the center plate portion 1041. The center plate portion 1041 has at its center a through-hole 1043 extending through the top surface and undersurface of the center plate portion 1041. The through-hole 1043 has on its inner surface at an upper end thereof an annular raised part (ridge) 1045. The inner diameter of the through-hole 1043 other than the annular raised part 1045 is substantially equal to the outer diameter of the cylindrical boss large-diameter lower end 1039, whereas the inner diameter of the annular raised part 1045 is slightly smaller than the outer diameter of the cylindrical boss large-diameter lower end 1039.

Although not shown, the center plate portion 1041 may comprise a plurality of fan-shaped grooves arranged surrounding the through-hole 1043 around the through-hole 1043. In this case, the cylindrical boss 1038 need not have the vertical cross groove 1040.

The slant plate portions 1042 of the lower member 1034 have on its top surface end sides engaging grooves 1047 corresponding in shape to the hook portions 1036 of the upper member 1033 so that, when the upper member 1033 is mounted on the lower member 1034, the hook portions 1036 of the upper member 1033 engage with the engaging grooves 1047 of the lower member 1034 to retain the lower member 1034.

Ends of the slant plate portion 1042 of the lower member 1034 has at their respective centers longitudinal notches 1048 so that when the upper member 1033 is mounted on the lower member 1034, the projections 1037 of the upper member 1033 engage with the notches 1048 of the lower member 1034 to restrict the width-direction movement of the upper member 1033 relative to the lower member 1034.

The thus configured pressing mechanism 1015 is assembled on the housing 1001 as shown in FIGS. 21 to 23. To be more specific, the lower structure 1017 is disposed in the center recess 910 of the housing 1001. The both end portions 1019 of the elastic expansion part 1018 of the upper structure 1016 is engaged with the longitudinal notches 1012 of the housing 1001 to retain the housing 1001 between these both end portions 1019. At this time, the user can assemble the upper structure 1016 and the housing 1001 together while abutting his/her thumb and forefinger against the notches 1014 of the housing 1001 to hold the housing.

Since the elastic expansion part 1018 is urged by the torsion spring 1022 such that the both end portions 1019 thereof come closer to each other, the housing 1001 is stably supported between the both end portions 1019. As shown, with the upper structure 1016 and the lower structure 1017 being assembled together, the undersurface of the coupling member 1031 is in contact with the top surface of the finger hold 1027, allowing the housing 1001 to be stably supported on the pressing mechanism 1015.

Upon attachment of the microneedle patch, as described above, the protective sheet affixed to the bottom surface of the housing 1011 is peeled off to expose the patch. The applicator 1000 is then placed on skin such that the peripheral base part of the housing 1011 abuts against skin. At this time, the both end portions 1019 of the elastic expansion part 1018 are in contact with skin.

Subsequently, the pressing mechanism 1015 is pressed against skin while abutting a finger (e.g. thumb) against the finger hold 1027 of the pressing mechanism 1015. This allows the both end portions 1019 of the elastic expansion part 1018 to be displaced outward in contact with skin, with its center portion being moved downward. In consequence, skin in the region confronting the microneedle patch is pulled in opposite directions. Accordingly, skin is subjected to a tension so that thereafter the microneedles easily stick into skin. Thus, skin is stretched out and resists against a pressure applied from a direction orthogonal to skin surface, resulting a state where a certain stress can be produced. When microneedle tips are pressed against skin surface in such a state, the microneedles can securely puncture skin surface.

Irregularities or grooves may be formed in the both end portions 1019 so as to increase the friction with skin or a pressure-sensitive adhesive may be disposed thereon.

According as the finger hold 1027 advances toward skin, the lower structure 1017 deforms the housing 1011 while pressing a recess center region 913 of the housing 1011. When the deformation of the housing 1011 proceeds, the slant plate portions 1042 of the lower member 103 are brought into contact with the recess end regions, respectively, so that the microneedles supported on the recess center region are strongly pressed against skin.

When a force is applied to the finger hold 1027, the upper member 1033 of the lower structure 1017 flexes at its center portion downward by a predetermined amount relative to the both side portions thereof; or the lower member 1034 flexes at its center portion upward by a predetermined amount relative to the both side portions thereof; or the upper member 1033 and the lower member 1034 flex at their center portions downward and upward, respectively, by a predetermined amount, with the result that the cylindrical boss 1038 of the upper member 1033 enters the through-hole 1043 of the lower member 1034. Then, when a previously determined given force is applied to the finger hold 1027, the lower end 1039 of the cylindrical boss 1038 gets over the raised part 1045 of the lower member 1034 so that the lower end 1039 of the cylindrical boss 1038 is engaged with the raised part (ridge) 1045 on the through-hole inner surface. The engagement of the lower end 1039 with the raised part 1045 is sensed by the user via a feeling of the finger in contact with the finger hold 1027 or via a sound. Therefore, the user can recognize that a predetermined force has been applied to the finger hold 1027. Application of a predetermined force to the finger hold 1027 allows the needles of the microneedle patch to enter into skin by a predetermined amount. As a result, drug carried on the needles can securely be administered to skin. In this manner, the cylindrical boss lower end portion 1039 and the raised part 1045 corresponding thereto act as an indicator that allows the user to sense that a predetermined force has been applied to the finger hold 1027.

When the force applied to the finger hold 1027 is weakened to become smaller than the predetermined force, the lower end portion 1039 of the cylindrical boss 1038 is disengaged from the raised part (ridge) 1045 on the through-hole inner surface due to the elastic recovery force of the upper member 1033 and the lower member 1034. The disengagement of the lower end portion 1039 from the raised part 1045 is sensed by the user via the finger placed on the finger hold 1027. Thus, the user can recognize that the predetermined force has not been persistently applied to the finger hold 1027. By causing the user to recognize in advance that the state where the lower end portion 1039 of the cylindrical boss 1038 is engaged with the raised part (ridge) 1045 on the through-hole inner surface should be maintained for a predetermined period of time, a required amount of drug can securely be administered to skin. This predetermined period of time may be described on instructions of the applicator 1000 for example so that a predetermined amount of drug can securely be administered to skin.

When the force applied to the finger hold 1027 is released, the elastic expansion part 1018 and the housing 1011 are restored to their respective pre-deformation shapes by their own elasticities.

The pressing mechanism 1015 and the housing 1001 may be engaged with each other by the user before use. Alternatively, without being engaged, the both end portions 1019 of the elastic expansion part 1018 and the longitudinal notches 1012 of the housing 1001 may be utilized or the positions may visually be confirmed so that positioning on skin, etc. is made in use.

Tenth Embodiment

Figure 25:
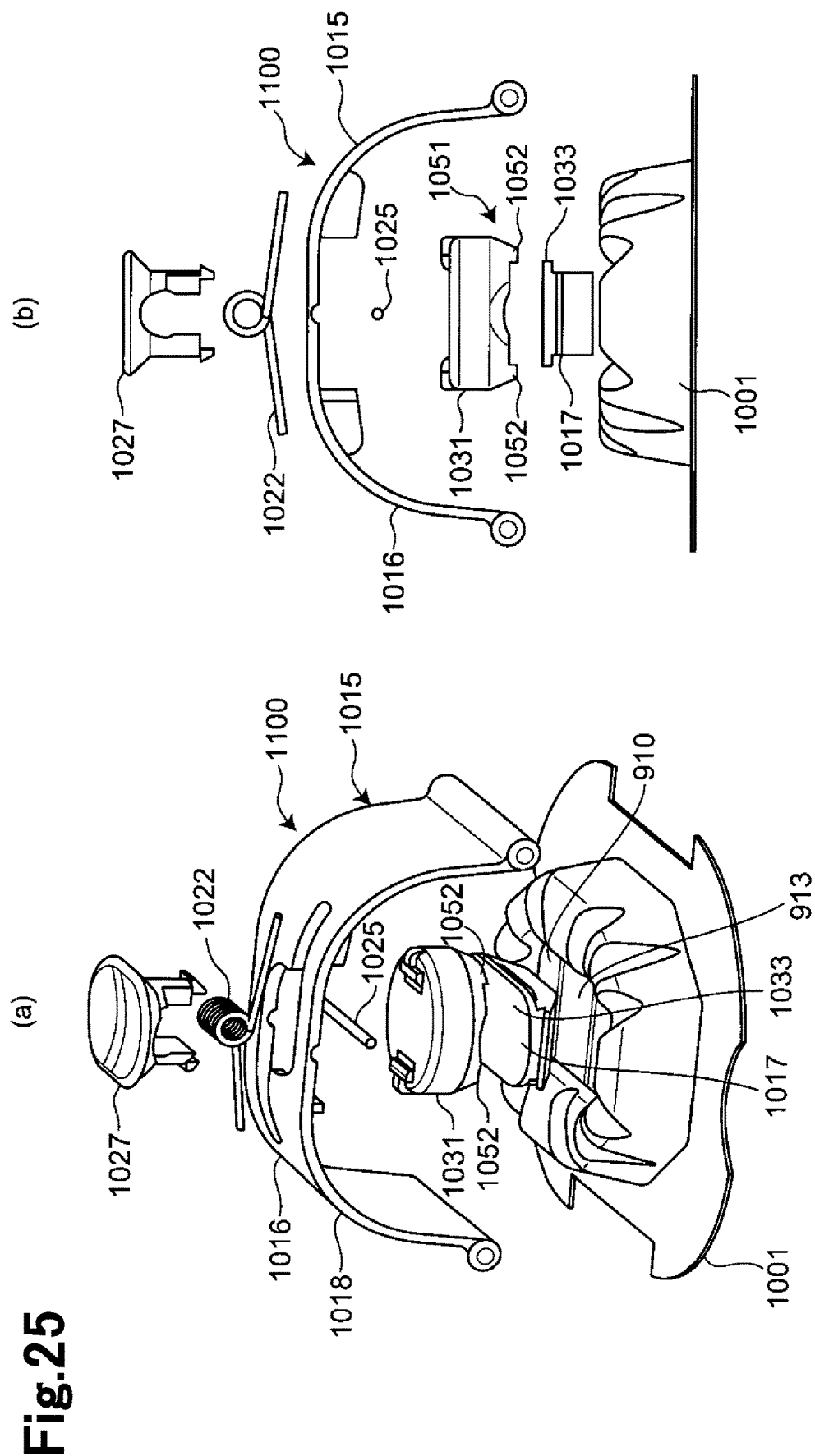
FIG. 25A is an upper, exploded perspective view of a microneedle patch applicator according to a tenth embodiment.
FIG. 25B is an exploded front view of the microneedle patch applicator according to a tenth embodiment.

FIG. 25 ((*a*) and (*b*) of FIG. 25) shows an applicator 1100 of a tenth embodiment. In the applicator 1100, the coupling member 1031 of the upper structure 1016 in the pressing mechanism 1015 comprises a coupling structure 1051 coupling the coupling member 1031 to the lower structure 1017. In the embodiment, the coupling structure 1051 comprises a pair of engaging hooks 1052 that are arranged symmetrically with respect to a vertical center axis of the coupling member 1031. The interval between the engaging hooks 1052 is designed to substantially equal to the short-side direction width of the lower structure upper member 1033 in the pressing mechanism so that the lower structure 1017 is retained in its entirety via the engaging hooks 1052 by the upper structure 1016. The other configurations are substantially the same as those of the ninth embodiment. Hence, the same members or the same portions are designated at the same reference numerals and will not again be described.

According to the applicator 1100 of the tenth embodiment configured in this manner, with the upper structure 1016 and the lower structure 1017 of the pressing mechanism 1015 being integrated, the pressing mechanism 1015 can easily be assembled to the housing 1001.

Eleventh Embodiment

Figure 26:
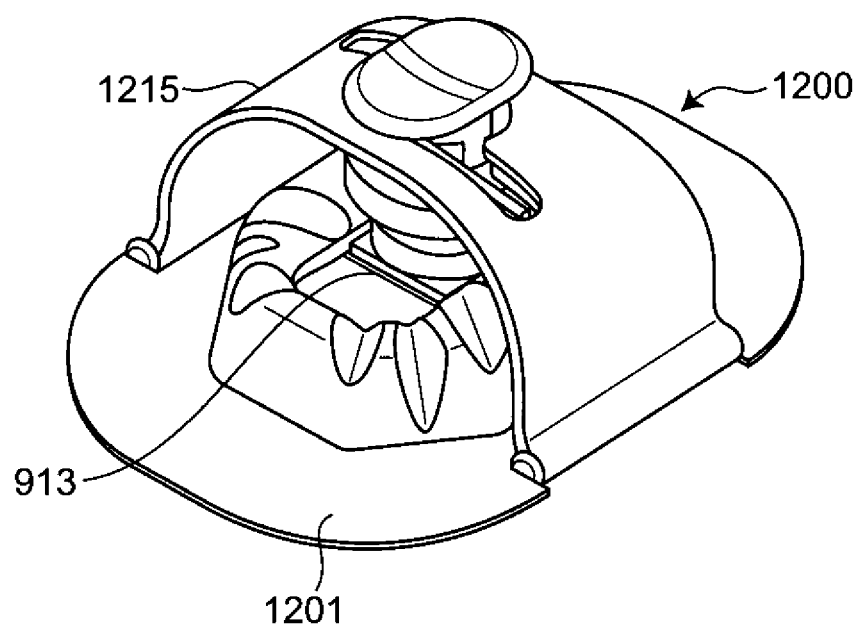
FIG. 26 is a perspective view of a microneedle patch applicator according to an eleventh embodiment.
Figure 27:
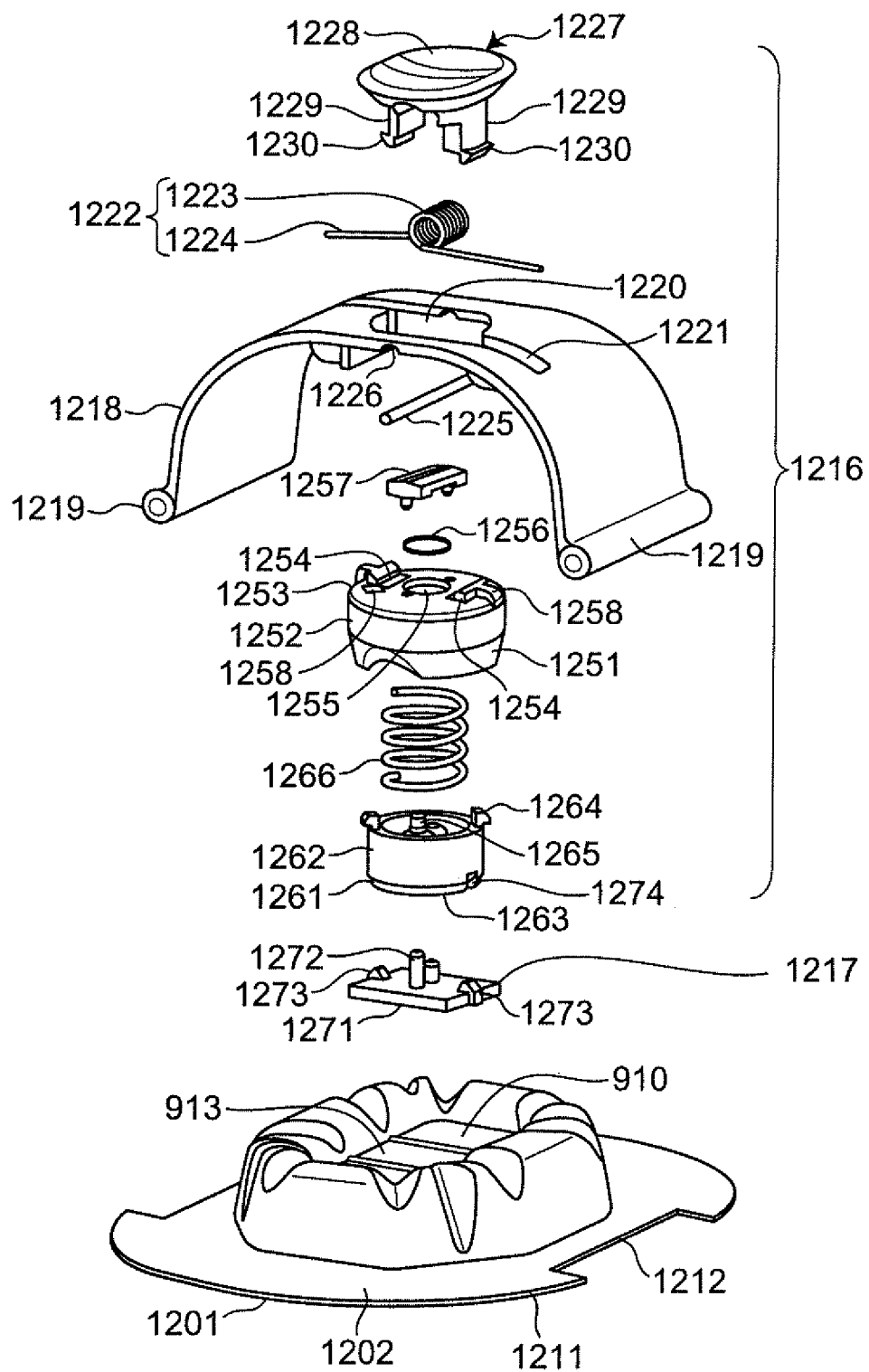
FIG. 27 is an exploded perspective view of the microneedle patch applicator according to the eleventh embodiment shown in FIG. 26.

FIGS. 26 and 27 show an applicator 1200 of an eleventh embodiment. The applicator 1200 comprises a housing 1201 and a pressing mechanism 1215.

As shown in FIG. 27, similarly to the ninth embodiment described above, the housing 1201 comprises a peripheral base part 1202. The peripheral base part 1201 has long-side-direction edges 1211 each having a notch 1212 in the shape of a bracket for example. Except for this, the housing 1201 is substantially the same as the housing 301 of the fourth embodiment. Hence, detailed description of the housing 1201 will not be repeated. In the following description, parts of the housing 1201 are appropriately designated at reference numerals of 900 s that are obtained by adding 600 to reference numerals imparted to corresponding parts of the housing of the fourth embodiment.

The pressing mechanism 1015 generally comprises an upper structure 1216 and a lower structure 1217. The upper structure 1216 comprises a substantially inverted-U-shaped or substantially inverted-arch-shaped elastic expansion part 1218. The elastic expansion part 1218 is made of e.g. a synthetic resin having an elasticity. Accordingly, when the elastic expansion part 1218 is subjected at its center portion to a force from above, the elastic expansion part 1218 can deform such that both end portions 1219 thereof move outward apart from each other. In the embodiment, the both end portions 1219 of the elastic expansion part 1218 are formed into a substantially cylindrical shape. In a free state, the interval between the left and right end portions 1219 is equal to or slightly greater than the distance between a pair of bracket-shaped notches 1212 formed in the long-side-direction edges 1211 of the housing 1201.

The elastic extension part 1218 has at its center region a substantially quadrangular opening 1220 extending through a top surface and an undersurface thereof. The top surface of the elastic expansion part 1218 includes a pair of grooves 1221 extending straight outward from diagonally confronting corners of the opening 1220 toward the both end portions 1219.

A torsion spring 1222 is stored in the opening 1220 and the grooves 1221. The torsion spring 1222 includes a winding portion 1223 of a wound wire and a pair of arm portions 1224 extending straight from both ends of the winding portion 1223. The thus configured torsion spring 1222 is retained via a pin 1225 on the elastic expansion part 1218, with the winding portion 1223 being stored in the opening 1220, with the arm portions 1224 being stored in the grooves 1221. The pin 1225 engages with the center undersurface of the elastic expansion part 1218 so that the winding portion 1223 is retained in the opening 1220 with the arm opening angle of the torsion spring 1222 being reduced, whereby the elastic expansion part 1218 is biased by the arm portions 1224 such that the both end portions 1219 thereof come closer to each other.

In the embodiment, the elastic expansion part 1218 has at its undersurface center a groove 1226 extending in the width direction in order to position the pin 1225, with the pin 1225 being stored in the groove 1226.

A finger hold 1227 is assembled on the elastic expansion part 1218. The finger hold 1227 includes an upper portion 1228 against which the user presses his/her finger (e.g. thumb) and a pair of legs 1229 extending downward from the undersurface of the upper portion 1228. Each of the legs 1229 has at its lower end an engaging portion 1230. The thus configured finger hold 1227 is assembled on the elastic expansion part 1218, with the winding portion 1223 of the torsion spring 1222 being clamped between the legs 1229, with the legs 1229 being inserted into the opening 1220 from above to below.

The lower end engaging portions 1230 of the legs 1229 projecting downward from the opening 1220 are engaged with and retained by a coupling member 1251. The coupling member 1251 is an inverted-pan-shaped member (in the shape of a pan turned upside down) having a cylindrical wall 1252 with a vertical center axis and a ceiling wall 1252 coupled to an upper end of the cylindrical wall 1252. The ceiling wall 1253 includes an axially symmetrical engaged portion 1254 that corresponds in shape to a finger hold lower end engaging portion 1230, with the finger hold lower end engaging portion 1230 being fitted in and engaging with the engaged portion 1254 so that the finger hold 1227 is coupled to the coupling member 1251.

The ceiling portion 1253 has at its center an inverted-truncated-cone-shaped opening 1255 (in the shape whose diameter gradually increases from the inner end toward the outer end). The opening 1255 stores a deformation member 1256 that includes a circular plate portion and a dish-like thin metal plate obtained by shaping the circumferential edge of the circular plate portion into an inverted-truncated-cone. In order to retain the deformation member 1256 in the opening 1255, the opening edge is of a shape corresponding to the circumferential edge inverted-truncated-cone shape, as described above.

The circular plate portion of the deformation member 1256 has a slightly downward convexly curved surface so that, for example, when the circular plate portion is pressed at its center portion from below toward above, the downward convexly curved surface warps into a concavely curved surface to produce a sound or a vibration at that time.

In order to retain the deformation member 1256 in the opening 255, a holding member 1257 is disposed on the deformation member 1256 and is fixed to the coupling member 1251. Fixing of the holding member 1257 to the coupling member 1251 can be performed for example by engaging an engaging protrusion formed on the holding member 1257 with an engaged portion formed on the coupling member 1251 correspondingly to the engaging protrusion.

In order to retain an ascending/descending member 1261 that will hereinafter be described, the coupling member 1251 has, at locations axially symmetrical with respect to the ceiling wall 1253, a pair of engagement holes 1258 extending through the top surface (outer surface) and the undersurface (inner surface).

The ascending/descending member 1261 is a pan-shaped member having a cylindrical wall 1262 with a vertical center axis and a bottom wall 1263 coupled to a lower end of the cylindrical wall 1262. The outer diameter of the ascending/descending member cylindrical wall 1262 is smaller than the inner diameter of the coupling member cylindrical wall 1252. The ascending/descending member collect wall 1262 has at its upper edge a pair of engagement portion 1264 that is axially symmetrically formed, while the ascending/descending member bottom wall 1263 has at its top surface center a pillar 1265 that extends upward.

For assembling, the thus configured ascending/descending member 1261 stores a coil spring 1266 in the inside thereof, with the ascending/descending member cylindrical wall 1262 being inserted into the coupling member cylindrical wall 1253 from below, with the engagement portion 1264 being engaged such that it can rise and lower through a groove or projection formed in the inner wall of the coupling member 1251. The axial (longitudinal) length of the coil spring 1266 is determined such that, with the coupling member 1251 and the ascending/descending member 1261 being assembled together, the coil spring 1266 is compressed between the ceiling wall 1253 and the bottom wall 1263 so that the ascending/descending member is urged toward and retained at a most lowered position (lowest position) with respect to the coupling member 1251.

The length of the pillar 1265 of the ascending/descending member 1261 is determined such that, in the state where the ascending/descending member 1261 lies at the lowest position with respect to the coupling member 1251 by the coil spring 1266 with the coupling member 1251 the ascending/descending member 1261 being combined together, the upper end of the pillar 1265 comes into light contact with or no contact with the center portion of the deformation member 1256.

The lower structure 1217 includes a quadrangular plate 1271 having substantially the same size as that of the recess center region 913 of the housing 1201. The plate 1271 has on its top surface at a center region at least one projection, with engaging portions 1273 being formed on confronting edges lying on both sides of the projection 1272. The thus configured plate 1271 is coupled to the ascending/descending member 1261 while engaging the projection 1272 and the engaging portions 1273 with a corresponding hole (not shown) formed in the ascending/descending member bottom wall 1263 and engaged portions 1274, respectively.

Upon attaching the microneedle patch, the protective sheet affixed to the bottom surface of the housing 1211 is peeled off to expose the patch. Since the protective seal has an easy peel function, it can easily be peeled off. The applicator 1200 is then placed on skin such that the peripheral base part of the housing 1211 abuts against skin.

Alternatively, when attaching the microneedle patch, the protective sheet affixed to the bottom surface of the housing 1211 is peeled off to expose the patch. Due to having an easy peel function, the protective sheet can easily be peeled off. The housing 1211 may then be coupled via the lower structure 1217 to the upper structure 1216, and the applicator 1200 may be placed on skin to abut the peripheral portion of the housing 1211 against skin.

Otherwise, upon attachment of the microneedle patch, the housing 1211 is coupled via the lower structure 1217 to the upper structure 1216, and then the protective sheet affixed to the bottom surface of the housing 1211 is peeled off to expose the patch. Afterword, the applicator 1200 may be placed on skin, and the peripheral portion of the housing 1211 may be abutted against skin.

Otherwise, the pressing mechanism 1215 may be engaged such that the plate 1271 of the lower structure 1217 is abutted against the recess 910 of the housing 1201 and such that the both ends 1219 of the elastic expansion part 1218 are positioned in the longitudinal notches 121 of the housing 1201.

In this state, the both end portions 1219 of the elastic expansion part 1218 are in contact with skin.

Succeedingly, the pressing mechanism 1215 is pressed against skin while abutting a finger (e.g. thumb) on the finger hold 1227 of the pressing mechanism 1215. This allows the both end portions 1219 of the elastic expansion part 1218 to be displaced outward in contact with skin while its center portion is moved downward. In consequence, skin in the region confronting the microneedle patch is pulled in opposite directions. Accordingly, skin is subjected to a tension so that thereafter the microneedles easily stick into skin.

According as the finger hold 1227 advances toward skin, the lower structure 1217 deforms the housing 1211 while pressing the recess center region 913 of the housing 1211. When the deformation of the housing 1011 proceeds, the microneedles supported on the recess center region are strongly pressed against skin.

When a predetermined force is applied to the finger hold 1227, the ascending/descending member 1261 ascends relative to the coupling member 1251, and the pillar 1265 pushes the deformation member 1256 at its center portion or central peripheral portion from below. As a result, the deformation member 1256 deforms from a downward convex state to a downward concave state, to produce a shock and a sound. This shock is sensed by the user through the finger placed on the finger hold 1227. Therefore, the user can recognize that a predetermined force has been applied to the finger hold 1227. Application of a predetermined force to the finger hold 1227 allows the needles of the microneedle patch to enter into skin by a predetermined amount. As a result, drug carried on the needles can securely be administered to skin. In this manner, the deformation member 1256 acts as an indicator that allows the user to sense that a predetermined force has been applied to the finger hold 1227.

When the force applied to the finger hold 1227 is weakened to become smaller than the predetermined force, the ascending/descending member 1261 and the pillar 1265 thereof return to the descent positions by an urging force of the coil spring 1266. As a result, the deformation member 1256 restores from the downward concave state to the downward convex state by its own elastic recovery force. Restoring of the deformation member 1256 to the downward convex state is sensed via a sound and a shock by the user through the finger placed on the finger hold 1227. Thus, the user can recognize that the predetermined force has not been persistently applied to the finger hold 1227. By causing the user to recognize in advance that the state of deformation of the deformation member 1256 should be maintained for a predetermined period of time, a required amount of drug can securely be administered to skin. This predetermined period of time may be described on instructions of the applicator 1200 for example so that a predetermined amount of drug can securely be administered to skin.

Figure 28:
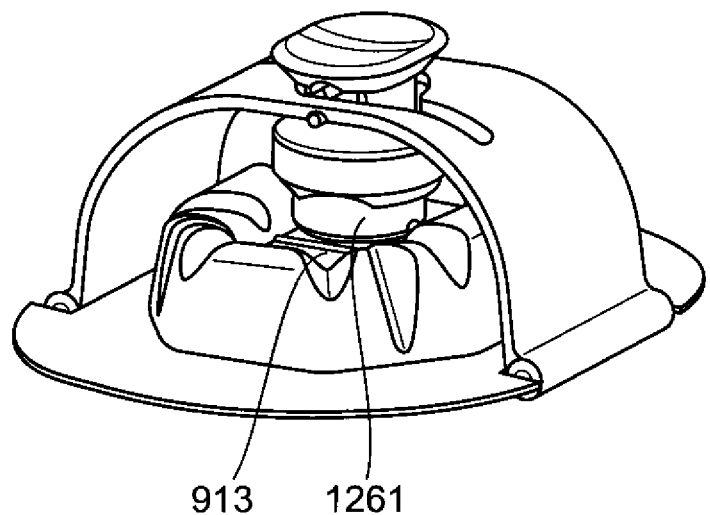
FIG. 28 is a perspective view of a microneedle patch applicator of another mode.
Figure 29:
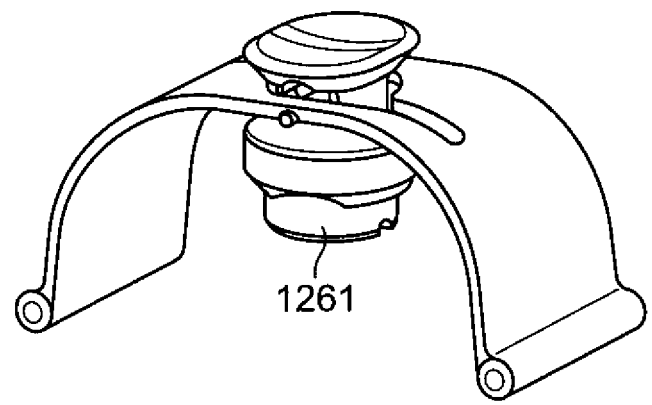
FIG. 29 is a partially exploded perspective view of the microneedle patch applicator shown in FIG. 28.
Figure 29:
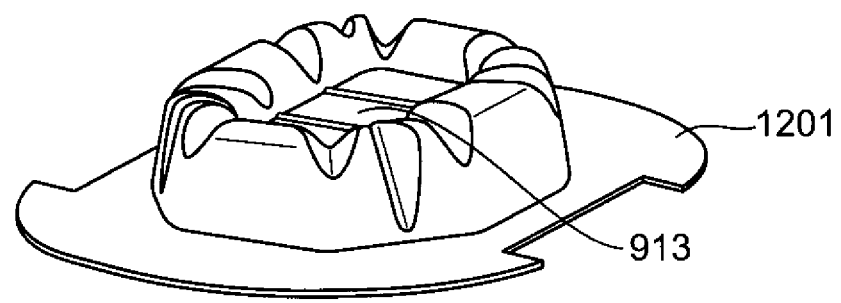

Although in the above eleventh embodiment the plate 1271 of the lower structure 1217 is fitted to the undersurface of the ascending/descending member 1261 to deform the housing 1201 via this plate 1271, the ascending/descending member 1261 may directly press the housing 1201 at the recess center portion 913 to deform the housing 1201, as shown in FIGS. 28 and 29.

The elastic expansion part 1218 of the pressing mechanism 1215 can control the spreading force due to the elasticity of the elastic expansion part itself and/or the resilience of the torsion spring, with the result that the force to spread skin can be maintained constant. Although the microneedles can easily be inserted by spreading skin and applying a tension, the state of skin differs at sites of skin or depending on individuals. By keeping constant the force to spread skin using this method, the differences based on the sites and individuals can be reduced so that the microneedles can be inserted into skin with a high accuracy.

Although in this specification the torsion spring has been exemplarily described as means urging the elastic expansion part, the torsion spring may be replaced by an elastic body such as a coil spring or a rubber, or a foam body.

The applicator of this disclosure may hermetically be packaged by a packaging material such as an aluminum laminate pouch having excellent light-shielding properties. The packaging container may hermetically contain agents such as a moisture absorbent and an oxygen absorbent for suppressing degradation of the microneedles and of drug carried thereon.

EXPLANATIONS OF LETTERS OR NUMERALS 1 microneedle patch applicator
11 housing
12 peripheral base part
13 raised part
14 outer edge
15 contour
16 long-side-direction contour part
17 short-side-direction contour part
18 long-side-direction side wall
19 short-side-direction side wall
20 upper end of long-side-direction side wall
21 upper end of short-side-direction side wall
22 long-side-direction tilted top-surface portion
23 short-side-direction tilted top-surface portion
24 boundary/concavely bent part
25 recess
26 circumferential wall
27 bottom
28 easy-to-deform part 29 center region
30 end region
31 finger hold
32 upper member
33 lower member
34 support
35 boss
36 end region (slant surface)
37 center region
38 protuberance
39 through-hole
40 microneedle patch
41 patch storage space
42 patch support surface
43 sheet substrate
44 microneedle array
45 substrate film
46 pressure-sensitive adhesive layer
47 release treatment layer (release layer)
48 base layer
49 needle
50 double-sided tape
55 protective sheet
56 deformation preventing member
1000 applicator
1001 housing
1011 long-side-direction edge
1012 notch
1013 short-side-direction edge
1014 notch
1015 pressing mechanism
1016 upper structure
1017 lower structure
1018 elastic expansion part
1019 end portion
1020 opening
1021 groove
1022 torsion spring
1023 winding portion
1024 arm portion
1025 pin
1026 groove
1027 finger hold
1028 upper portion
1029 leg
1030 engaging portion
1031 coupling member
1032 recess
1033 upper member
1034 lower member
1035 platform
1036 hook portion
1037 projection
1038 cylindrical boss
1039 lower end
1040 vertical groove
1041 center plate portion
1042 slant plate portion
1043 through-hole
1045 raised part (ridge)
1047 engaging groove
1048 notch
1051 coupling structure
1052 engaging hook
1200 applicator
1201 housing
1211 long-side-direction edge
1212 notch
1215 pressing mechanism
1216 upper structure
1217 lower structure
1218 elastic expansion part
1219 end portion
1220 opening
1221 groove
1222 torsion spring
1223 winding portion
1224 arm portion
1225 pin
1226 groove
1227 finger hold
1228 upper portion
1229 leg
1230 engaging portion
1251 coupling member
1252 cylindrical wall
1253 ceiling wall
1254 recess
1255 opening
1256 deformation member
1257 engagement hole
1261 ascending/descending member
1262 cylindrical wall
1263 bottom wall
1264 engagement portion
1265 pillar
1266 coil spring
1071 plate
1272 projection
1273 engaging portion

The invention claimed is:

1. A microneedle patch applicator housing,
the housing being formed from a single sheet or film having a top surface and an undersurface,
the housing comprising a flat peripheral base part and a raised part surrounded by the peripheral base part and bulging vertically, with respect to the peripheral base part, from the undersurface toward the top surface,
an undersurface portion of the raised part forming a surface supporting a microneedle patch,
the raised part including a plurality of concavely bent parts,
the concavely bent parts each having a concave bottom extending radially, when viewed from above, from corners of the raised part toward corners of a center region of the raised part.

2. The microneedle patch applicator housing of claim 1, wherein
the concavely bent parts are arranged symmetrically with respect to two horizontal axes (x-axis and y-axis) that are orthogonal to a vertical axis (z-axis) extending through a center of the raised part and that are orthogonal to each other.

3. The microneedle patch applicator housing of claim 1, wherein
the concavely bent parts are arranged with a rotational symmetry (n-fold symmetry: n is an integer greater than or equal to 2).

4. The microneedle patch applicator housing of claim 1, wherein
the raised part is shaped symmetrical with respect to at least one of the two horizontal axes (x-axis and y-axis).

5. The microneedle patch applicator housing of claim 1, wherein the raised part is shaped symmetrical with respect to the two horizontal axes (x-axis and y-axis).

6. The microneedle patch applicator housing of claim 1, wherein
the raised part is shaped with a long axis (x-axis) that is one of the two horizontal axes (x-axis and y-axis) and with a short axis (y-axis) that is the other of the two horizontal axes.

7. The microneedle patch applicator housing of claim 1, wherein
the raised part is rotationally symmetrical (n-fold symmetry: n is an integer greater than or equal to 2) with respect to a vertical axis (z-axis) extending through a center of the raised part.

8. The microneedle patch applicator housing of claim 1, wherein
the raised part has a recess at a center thereof, and wherein
an undersurface portion of the recess forms a surface supporting the microneedle patch.

9. The microneedle patch applicator housing of claim 1, comprising a ridge extending along a contour of the raised part and surrounding the recess, wherein
the ridge comprises a plurality of concavely bent parts.

10. The microneedle patch applicator housing of claim 9, wherein
the contour is shaped symmetrical with respect to the two horizontal axes (x-axis and y-axis).

11. The microneedle patch applicator housing of claim 9, wherein
the contour is shaped with a long axis (x-axis) that is one of the two horizontal axes (x-axis and y-axis) and with a short axis (y-axis) that is the other of the two horizontal axes.

12. The microneedle patch applicator housing of claim 9, wherein
the contour is rotationally symmetrical (n-fold symmetry: n is an integer greater than or equal to 2) with respect to the vertical axis (z-axis).

13. The microneedle patch applicator housing of claim 8, wherein
the recess includes a flat surface,
the flat surface having two easy-to-deform parts that are arranged symmetrically with respect to the short axis and that extend parallel to the short axis (y-axis),
the flat surface including a center region interposed between the two easy-to-deform parts and end regions positioned on both sides of the center region.

14. The microneedle patch applicator housing of claim 2, wherein
the raised part is disposed continuously circumferentially around the vertical axis (z-axis).

15. The microneedle patch applicator housing of claim 1, wherein
at least one or more of the plurality of concavely bent parts have a concave bottom sloped downward toward a direction away from a center portion of the raised part.

16. A microneedle patch applicator comprising:
the microneedle patch applicator housing of claim 1; and
a microneedle patch supported on a surface that supports the microneedle patch.

17. The microneedle patch applicator of claim 16, wherein
the recess comprises a finger hold.

18. The microneedle patch applicator of claim 16, wherein
a protective sheet is affixed to an undersurface of the housing, and wherein
the protective sheet closes an opening of a pad storage space formed at the back of the raised part.

19. The microneedle patch applicator of claim 16, wherein
the finger hold comprises an indicator indicating that a predetermined force is applied to the finger hold.

20. The microneedle patch applicator housing of claim 2, wherein the raised part is diposed discontinuously circumferentially around the vertical axis.

* * * * *